US009095251B2

(12) United States Patent
Purks et al.

(10) Patent No.: US 9,095,251 B2
(45) Date of Patent: Aug. 4, 2015

(54) CIRCUITS, SYSTEMS, AND METHODS FOR MONITORING AND COACHING A PERSON'S SIDEWAYS SPACING FOOT PLACEMENT AND ROLL, SHOE LIFE, AND OTHER RUNNING/WALKING CHARACTERISTICS

(71) Applicants: Bryce Benjamin Purks, Cary, NC (US);
Connor Kent Purks, Cary, NC (US);
Kory Patrick Purks, Cary, NC (US);
Deborah Rhea Purks, Cary, NC (US);
David Kent Purks, Cary, NC (US)

(72) Inventors: Bryce Benjamin Purks, Cary, NC (US);
Connor Kent Purks, Cary, NC (US);
Kory Patrick Purks, Cary, NC (US);
Deborah Rhea Purks, Cary, NC (US);
David Kent Purks, Cary, NC (US)

( * ) Notice: Subject to any disclaimer, the term of this patent is extended or adjusted under 35 U.S.C. 154(b) by 0 days.

(21) Appl. No.: 14/076,405

(22) Filed: Nov. 11, 2013

(65) Prior Publication Data

US 2014/0062703 A1    Mar. 6, 2014

Related U.S. Application Data

(63) Continuation-in-part of application No. 12/932,056, filed on Feb. 16, 2011, now Pat. No. 8,581,731.

(51) Int. Cl.
| | |
|---|---|
| *G08B 23/00* | (2006.01) |
| *A61B 5/00* | (2006.01) |
| *A61B 5/103* | (2006.01) |
| *G01P 15/18* | (2013.01) |
| *A61B 5/22* | (2006.01) |
| *A61B 5/11* | (2006.01) |

(52) U.S. Cl.
CPC ............. *A61B 5/0002* (2013.01); *A61B 5/1036* (2013.01); *A61B 5/1038* (2013.01); *A61B 5/1122* (2013.01); *A61B 5/22* (2013.01); *G01P 15/18* (2013.01); *A61B 2562/0219* (2013.01)

(58) Field of Classification Search
CPC .. A61B 5/1036; A61B 5/1038; A61B 5/1116; G01P 15/18; A63B 23/035
USPC ........... 340/573.1, 573.7, 665; 73/865.4, 488, 73/510; 702/150, 160
See application file for complete search history.

(56) References Cited

U.S. PATENT DOCUMENTS

| | | | | |
|---|---|---|---|---|
| 6,301,964 | B1 * | 10/2001 | Fyfe et al. ..................... | 73/865.4 |
| 6,305,221 | B1 | 10/2001 | Hutchings | |
| 6,513,381 | B2 * | 2/2003 | Fyfe et al. ..................... | 73/865.4 |
| 7,355,519 | B2 | 4/2008 | Grold et al. | |
| 7,827,000 | B2 | 11/2010 | Stirling et al. | |
| 7,911,339 | B2 | 3/2011 | Vock et al. | |
| 7,912,672 | B2 | 3/2011 | Feichtinger et al. | |
| 8,581,731 | B2 * | 11/2013 | Purks et al. ................. | 340/573.7 |
| 8,739,639 | B2 * | 6/2014 | Owings et al. ........... | 73/862.046 |
| 2012/0041767 | A1 | 2/2012 | Hoffman et al. | |
| 2014/0195023 | A1 * | 7/2014 | Statham et al. ................. | 700/91 |

* cited by examiner

Primary Examiner — John A Tweel, Jr.

(57) ABSTRACT

A foot monitoring system includes a measurement circuit and an alert circuit. The measurement circuit measures sideways roll of a person's foot while the person is walking/running. The alert circuit determines that the person should change sideways spacing between the person's feet to change further measured values of the sideways roll of the person's foot toward preferred sideways roll values, and generates a notification that indicates to the person to change the sideways spacing between the feet. The foot measurement circuit may determine how much shoe cushioning life remains for a shoe worn by the person in response to comparison of values a peak pulse segment of impact measurements to another segment of the impact measurements that is outside the peak pulse segment.

17 Claims, 24 Drawing Sheets

CIRCUITS, SYSTEMS, AND METHODS FOR MONITORING AND COACHING A PERSON'S SIDEWAYS SPACING FOOT PLACEMENT AND ROLL, SHOE LIFE, AND OTHER RUNNING/WALKING CHARACTERISTICS

CROSS REFERENCE TO RELATED APPLICATION

The present application claims the benefit of priority as a continuation-in-part application from U.S. patent application Ser. No. 12/932,056 filed Feb. 16, 2011, entitled "CIRCUITS, SYSTEMS, AND METHODS FOR MONITORING AND REPORTING FOOT IMPACT, FOOT PLACEMENT, SHOE LIFE, AND OTHER RUNNING/WALKING CHARACTERISTICS," the disclosure of which is hereby incorporated herein in its entirety by reference.

FIELD OF THE INVENTION

This invention relates to monitoring athletic activity, and more particularly to apparatuses and methods for monitoring running activities.

BACKGROUND OF THE INVENTION

Over the course of a 5-K run, the average runner strikes the ground about 3,000 times, placing ground reaction force loads of 2 to 3 times the body weight on each leg and sending shock waves through the feet, legs, spine, and elsewhere. Because of this repetitive high-impact loading, many injuries are associated with running. The injuries can include "runner's knee" (pain in the knee), Shin splints, bone stress fractures, plantar fasciitis, and Achilles tendinitis. Repetitive stress in the same tissues/bones without enough time for recovery or running with improper form can lead to such injuries.

The advice generally given to runners to attempt to avoid such injuries is to warm up before exercising, use cross training with different speeds/distances/exercises as part of an exercise routine, run on softer surfaces, use high-quality cushioned running shoes, and to replace running shoes often. Because the cushioning provided by running shoes wears out over time, avid runners are generally advised to replace running shoes every six months. In view of the high cost of quality running shoes, runners are presented with a dilemma of balancing the replacement cost of shoes with essentially a guesstimate as to when a particular pair of running shoes no longer provides sufficient cushioning and should be replaced before injury. Once a pair of shoes is replaced, it generally is never used again for running, although it may still provide sufficient cushioning for running on softer surfaces, such as on treadmills, gravel/dirt, or grass.

Consequently, there continues to be a tremendous need for further innovation that can assist runners with avoiding preventable injuries while enabling more cost effective use of running shoes.

SUMMARY OF THE INVENTION

Various embodiments of the present invention are directed to a foot impact monitoring system that functions as a electronic virtual running/walking coach that enables a person to more accurately and effectively regulate foot impact, improving foot placement, and/or determine remaining shoe life. The system can notify a person as to how hard the person's feet have been impacting a surface, notify the person as to whether the person's feet are impacting a surface at a proper relative distance from the body, and/or notify the person as to how much cushioning life remains in a pair of shoes. When the notifications are provided to the person during the running/walking activity, the person can respond by taking immediate actions to adjust the foot placement relative to the body and/or adjust the level of foot impact to an acceptable level by varying the speed, step distance, and/or posture while running/walking and/or by selecting among different available surfaces (e.g., concrete, treadmills, gravel/dirt, rubber coated, grass) on which to run/walk. A person may also more accurately determine when a particular pair of shoes should be replaced because they no longer provide a sufficient level of cushioning to compensate for the levels of foot impact that are occurring.

In some embodiments, a foot impact monitoring system includes an impact measurement circuit and an impact alert circuit. The impact measurement circuit is configured to measure impact from a foot repetitively striking a surface while a person is walking/running. The impact alert circuit is configured to respond to the measured impact by generating for the person an indication of how much impact is occurred from the foot striking the surface.

In some further embodiments, the impact alert circuit regulates a background sound component in response to a measured level of the impact, and combines the background sound component with a music component generated by a music player to generate a combined signal that is played to the person to audibly indicate to the person how much impact occurred from the foot striking the surface.

The impact alert circuit may be configured to increase loudness of the background sound component relative to the music component of the combined signal being played to the person in response to a presently measured level of the impact exceeding a baseline threshold level by an increased amount to audibly indicate to the person when the level of impact from the foot striking the surface has increased. Conversely, the impact alert circuit may decrease loudness of the background sound component relative the music component of the combined signal being played to the person in response to a presently measured level of the impact exceeding the baseline threshold level by a decreased amount to audibly indicate to the person when the level of impact from the foot striking the surface has decreased.

In some further embodiments, a sound generation device is configured to generate sound to the person. The impact alert circuit is further configured to generate a baseline threshold level in response to an average of measurements of the levels of impact, and to respond to a presently measured level of the impact exceeding the baseline threshold level by causing the sound generation device to generate a foot impact warning sound to the person.

The impact alert circuit may increase loudness and/or modify a defined tone characteristic of the foot impact warning sound generated by the sound generation device in response to a presently measured level of the impact exceeding the baseline threshold level by an increased amount to audibly indicate to the person when the level of impact from the foot striking the surface has increased. Conversely, the impact alert circuit may decrease loudness and/or oppositely modify the defined tone characteristic of the foot impact warning sound generated by the sound generation device in response to a presently measured level of the impact exceeding the baseline threshold level by a decreased amount to audibly indicate to the person when the level of impact from the foot striking the surface has decreased.

In some further embodiments, the foot impact monitoring system includes a display device that is configured to display indicia to the person. The impact alert circuit generate a record of the measured levels of impact and communicate the record of the measured levels of impact to the display device. The display device, via the impact alert circuit, graphs the measured levels of impact from the record relative to an elapsed time of the activity, a speed at which the person was walking/running, and/or a distance that the person walked/ran.

In some further embodiments, the impact alert circuit is configured to monitor the measured impact while the person is walking/running over the life of at least one of the person's shoes, and to generate an indication of when the shoe has become worn-out in response to how much the monitored impact measurements change over the life of the shoe. The impact alert circuit may respond to a calibration signal from a person by generating a baseline threshold level in response to an average of measurements of the levels of impact, and may generate an indication of when the shoe has become worn-out in response to how much the monitored acceleration measurements change relative to the baseline threshold level.

The impact alert circuit may be configured to respond to a calibration signal from a person by generating a baseline threshold level in response to an average of a rate of change of measurements of the levels of impact, and to generate an indication of when the shoe has become worn-out in response to a comparison of a rate of change of a present measurement of the level of impact to the baseline threshold level.

In some further embodiments, the impact alert circuit is further configured to determine from characteristics of the measured impact when the person is placing the foot excessively forward when striking the surface and resulting in excessive undesirable slowing forces exerted on the foot and retarding forward movement of the person. The impact alert circuit can generate an audible/visual warning to the person that an improper foot placement condition exists responsive to the determination that the person is placing the foot excessively forward when striking the surface. The impact alert circuit may determine that the person is placing the foot excessively forward when striking the surface in response to determining from the measured impact when acceleration greater than a defined threshold occurs in a direction opposite to a forward direction of movement of the person.

In some further embodiments, the impact alert circuit is further configured to determine from characteristics of the measured impact when the person is leaning the foot (ankle) inward (pronation) or outward (supination) when striking the surface and resulting in undesirable rotational forces exerted on the foot, ankle, and/or knee. The impact alert circuit can generate an audible/visual warning to the person that notifies the person of the foot leaning contact and may further provide an indication of the extent of the leaning (e.g., indicate supination (underpronation), neutral pronation, or overpronation).

Another embodiment of the foot measurement system includes a measurement circuit and an alert circuit. The measurement circuit measures sideways roll of a person's foot during at least a portion of forward rolling progression as the foot rolls forward from an impact location to lift-off from a running surface while the person is walking/running. The alert circuit determines based on the sideways roll that the person should change sideways spacing in a sideways direction between forward paths of the person's feet to change further measured values of the sideways roll of the person's foot toward preferred sideways roll values of the person's foot while the person continues walking/running. The alert circuit also generates a notification that indicates to the person to change the sideways spacing in the sideways direction between forward paths of the person's feet while the person continues walking/running.

Another embodiment of the foot measurement system includes a measurement circuit and an alert circuit. The measurement circuit measures impacts from a foot repetitively striking a surface while a person is walking/running. The alert circuit monitors the measured impacts while the person is walking/running. The alert circuit compares a peak pulse segment of measurements of at least one impact to another segment of measurements that is outside the peak pulse segment of the measurements of the at least one impact, and generates a notification that indicates to a person how much shoe cushioning life remains for a shoe worn by the person in response to the comparison of values the peak pulse segment of the measurements of the at least one impact to the other segment of the measurements that is outside the peak pulse segment of the measurements of the at least one impact.

Additional apparatuses and methods according to other embodiments of the invention will be or become apparent to one of skill in the art upon review of the following drawings and Detailed Description. It is intended that all such additional apparatus and methods be included within this description, be within the scope of the present invention, and be protected by the accompanying claims.

BRIEF DESCRIPTION OF THE DRAWINGS

The accompanying drawings, which are included to provide a further understanding of the invention and are incorporated in and constitute a part of this application, illustrate certain embodiments of the invention. In the drawings.

DETAILED DESCRIPTION

Figure 1:
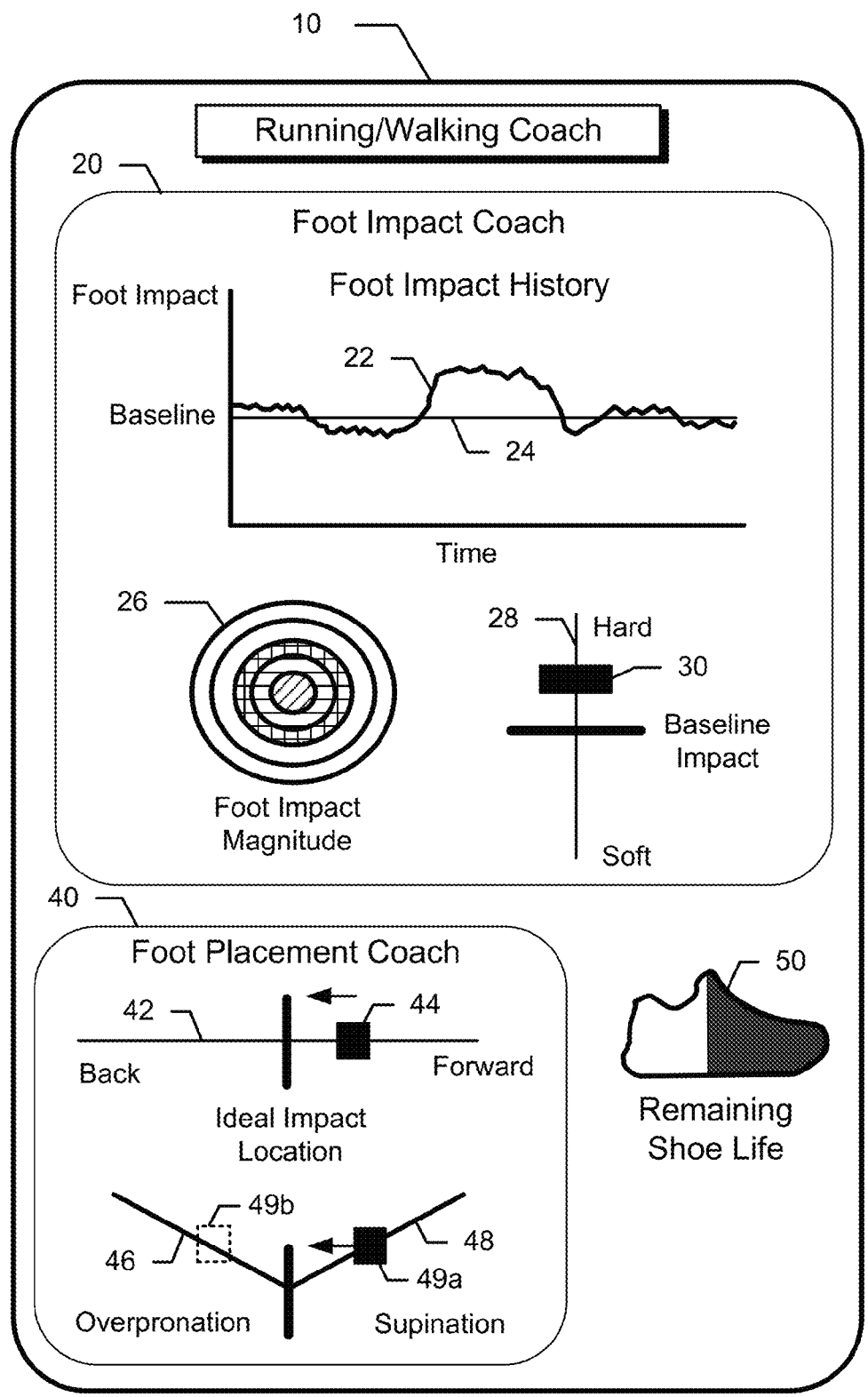
FIG. 1 illustrates example information that can be generated by a foot impact monitoring system for display on a display device to coach a runner/walker on reducing foot impact, improving foot placement, and/or advising as to remaining shoe life according to some embodiments of the present invention.

Embodiments of the present invention now will be described more fully hereinafter with reference to the accompanying drawings, in which embodiments of the invention are shown. This invention may, however, be embodied in many different forms and is not be construed as limited to the embodiments set forth herein.

As explained above, many injuries are associated with running. While running, fatigue and other physiological changes (e.g., endorphins, aka "runner's high") can mask pain and other warning signs from bad running form, such as from excessively hard foot impact (e.g., stomping) and/or improperly impacting their feet too far ahead of the body. Bad running form can create high impact forces and/or vibration transmitted through the runner's shoes into the feet, legs, and body. These forces and vibration can cause "runner's knee" (pain in the knee), Shin splints, bone stress fractures, plantar fasciitis, Achilles tendinitis, back pain, etc.

Although runners are advised to frequently replace their running shoes to attempt to obtain sufficient cushioning, runners must balance the risk of injury with their guesstimate as to when a particular pair of running shoes no longer provides sufficient cushioning and needs replacement.

Various embodiments of the present invention are directed to an electronic foot impact monitoring system that functions as a running/walking coach that provides information to a runner/walker as to how hard their feet are impacting a surface, whether they are running/walking with proper foot placement relative to their body (e.g., foot impact too far ahead of body, rear foot impact, midfoot impact, forefoot impact), and/or determine and display how much useful cushioning life remains in shoes.

Various embodiments are described herein in the example context of providing real-time information to a person who is running/walking as to how the person's feet are impacting a surface so the person can adjust how hard the feet are impacting surface, can change what type of surface is run on (e.g., concrete, treadmills, gravel/dirt, rubber coated track, grass, etc.), can adjust where the feet are impacting the surface relative to their body (e.g. adjust how far ahead of their body), and/or determine when a particular pair of running shoes is nearing or has reached the end of its useful cushioning life. However, these embodiments are not limited to providing real-time information, and may additionally or alternatively be embodied in a foot impact monitoring system that provides information to the person after completion of a run/walk, such as by post-operations on a desktop computer, laptop computer, palmtop computer, tablet computer, smart phone, or other electronic device that may or may not be carried by the person while running/walking.

As used herein, the term "foot impact" refers to acceleration, rate of change or acceleration (e.g., jerk), force, and/or pressure that is applied to a foot responsive to striking a surface while running, walking, and/or jumping.

FIG. 1 illustrates an example informational display 10 that is generated on a display device to provide coaching to a runner/walker according to some embodiments of the present invention. Referring to FIG. 1, the informational display 10 can function as a foot impact coach and/or foot placement coach using information generated by a foot impact monitoring system as will be described below with regard to FIGS. 2-18. It is to be understood that the particular embodiments of FIG. 1 are provided as illustrative examples only, and that the invention is not limited thereto. Other information may be selected for display and may be displayed in other orientations and/or formats to provide the recited function of informing a person as to foot impact levels and/or foot placement.

Foot impact information display(s) 20 may include a foot impact history graph 22 that plots measured levels of foot impact while a person is running/jogging relative to a timeline. The impact history graph 22 may include a baseline threshold level 24 that is generated in response to an average of impact level measurements and/or which was set during a calibration process. For example, the foot impact monitoring system may determine the baseline threshold level 24 by averaging impact level measurements over a sufficient period of time (e.g., more than one minute) to develop a typical impact level for the particular person while running/walking at a typical speed, stride, etc. and for a particular pair of shoes. In some embodiments, the average impact level 24 is generated in response to the person triggering the foot impact monitoring system to enter a calibration mode during which a new/different pair of shoes is used to run at least a defined/suggested distance (e.g., several hundred feet or, in some embodiments, at least one mile) to develop a typical impact level for that person running/walking with the particular shoes. A person may additionally or alternatively trigger the foot impact monitoring system while running at a preferred foot impact level, speed, and/or stride and/or while running on a particular type of running surface (e.g., grass, treadmill, pavement, rubber surface track etc) to set the baseline 24 to which subsequent foot impact measurements can be compared against.

Accordingly, a person can view the foot impact history graph 22 to determine whether the person's feet are impacting the surface harder or softer relative to the baseline threshold level 24, and may thereby take actions to adjust the level of foot impact to a desired level, such as by adjusting the foot placement relative to the body, the speed, the step distance, and/or posture while running/walking, and/or by selecting among different available surfaces (e.g., concrete, treadmills, gravel/dirt, rubber coated, grass) on which to run/walk. When the foot impact monitoring system is carried by the person while running/walking, the person may dynamically view the impact history graph 22 and make adjustments so as to immediately provide an acceptable level of foot impact for the person.

The foot impact information display(s) 20 may alternatively or additionally include other types of graphical display of the present level of foot impact magnitude. For example, a present measurement of foot impact may be indicated by selectively shading concentric circles 26, with the innermost circle being shaded to indicate a relatively soft foot impact and successive outer circles being shaded to indicate that increases in foot impacts are occurring, or vice versa. Accordingly, a measured foot impact that is less than a first threshold can be indicated by shading the innermost circle, an impact that is greater than the first threshold and less than a larger second threshold communicated by shading the next radial outward circle, an impact that is greater than the second threshold and less than a less than a larger third threshold communicated by shading the next radial outward circle, and so on with threshold increases in foot impact causing further outward circles to be shaded, or vice versa (e.g., shading from the outmost circuit inward responsive to threshold measurement increases in foot impact).

The foot impact information display(s) 20 may alternatively or additionally include a linear graph 28 that illustrates a relative strength of a present foot impact. The graph 28 may illustrate a marker 30 that represents a present level of foot impact that has been measured while a person is running/walking, and which may be illustrated relative to a baseline impact level that may defined as described above for the baseline threshold level 24 or elsewhere for other determined baseline threshold level(s).

Accordingly, a person can view the concentric circles 26 and/or the linear graph 28 to determine whether the person's feet are impacting the surface harder or softer than desired, and may take immediate actions to adjust the level of foot impact to a desired level, such as by adjusting the foot placement relative to the body, the speed, the step distance, and/or posture while running/walking, and/or by selecting among different available surfaces on which to run/walk.

The foot impact information display(s) 20 may alternatively or additionally include a foot placement informational display 40 that can function as a foot placement coach while a person is running/walking or to provide useful feedback after completing the activity. The foot placement informational display 40 may for example include a linear graph 42 that illustrates a marker 44 that represents a present location of where the foot is striking a surface relative to an ideal impact location. The ideal impact location may be calibrated to correspond to a location relatively near the person's body that reduces backward impact forces against the feet and/or provides a desired foot strike location on the feet (e.g., rear foot, midfoot, forefoot strike location). When the foot impact monitoring system is carried by the person while running/walking, the person may dynamically view the foot placement informational display 40 and make adjustments to where the person's feet are striking the surface to avoid unnecessary impact forces/vibration on person's muscular, tendon, and skeletal structure of the feet, legs, and body.

The foot placement informational display 40 may alternatively or additionally provide information on whether the person is running/walking with overpronation or supination when the feet are impacting the surface, and may further indicate a relative amount of overpronation or supination that is occurring. For example, the information display 40 may include a graph 46,48 with a movable marker 49 that is moved along the graph 46,48 to indicate whether and to what extent the foot is impacting a surface with overpronation (distance of marker 49a along line 46 from ideal foot plant angle represented by vertical line), and to indicate whether and to what extent the foot is impacting a surface with supination (distance of marker 49b along line 48 from ideal foot plant angle represented by vertical line). The ideal foot plant angle may be calibrated for a particular person to compensate for the unique skeletal-muscular structure of a person that dictates what is a comfortable foot plant angle for that person. The calibration may be carried out in response to a user command while the person while running/walking with a comfortable foot placement, or may be carried out as an average or other numeric combination of sensed impact valued over a defined time period.

With a normal pronation (e.g., indicated by the vertical line) foot placement, the outside part of the heel makes initial contact with the ground. The foot "rolls" inward (e.g., about fifteen percent) and comes in complete contact with the ground. The rolling in of the foot optimally distributes the forces of impact, and is an important movement for proper impact absorption.

With an overpronation foot placement (e.g., marker 49b shown along line 46), the outside of the heel makes the initial ground contact and then the foot rolls inward more than an ideal amount (e.g., more than fifteen percent). Overpronation can cause the foot and ankle to have problems stabilizing the body, and provide poor impact absorption, and at the end of the gait cycle, the front of the foot pushes off the ground using mainly the big toe and second toe, which then must do all the work.

With a supination (underpronation) foot placement (e.g., marker 49a shown along line 48), the outside of the heel makes initial contact with the ground and then inward movement of the foot occurs at less than an ideal amount (e.g., less than fifteen percent), with resulting forces of impact being concentrated on a smaller area of the foot (the outside part) and not efficiently distributed. In the push-off phase, most of the work is done by the smaller toes on the outside of the foot.

The foot impact information display(s) 20 may alternatively or additionally include indicia that indicate when a particular pair of running shoes no longer provides sufficient cushioning and should be replaced before onset of occurrence of one or more running related injuries. For example, a shoe outline (or other graphical object) 50 can be filled-in (or emptied) to graphically indicate how much cushioning life remains in a particular pair of shoes. A filled-in shoe outline 50 (or emptied outline) may thereby indicate that the shoes should be replaced because they no longer provide a sufficient level of cushioning.

The information display 10 of FIG. 1 is provided as a non-limited example to illustrate various embodiments and does not limit the scope of the invention. It is to be understood that history graphs may be provided for various other analysis of the foot impact display 20 (e.g., history graphs may be provided instead of or in addition to the graphs 26 and 28), and may be graphed relative to time, distance run/walked, speed, stride step distance, etc to allow a person to develop an understanding of how their foot impact measurements can vary with the various running/walking parameters. For example, the person may be able to determine from the displayed information that their foot impact becomes excessive at certain running speeds, such as due to a longer stride step distance, and can therefore adapt their running speed or allowed duration at that speed when running/walking on some types of surfaces based on that information. The person may alternatively or additionally determine from the displayed information that their foot impact is excessive during a warm-up phase of running, such as due to insufficient stretching, or near the end of a run, such as due to fatigue, and may thereby adapt their warm-up phase or end-run phase (e.g., select a softer running surface, run at a speed/stride distance that provides lower impact) to reduce the foot impact.

It is to be further understood that time history graphs may be provided for various other analysis of the foot placement displays 40 (e.g., history graphs may be provided instead of or in addition to the graphs 42 and 46,48), and may be graphed relative to time, distance run/walked, speed, stride step distance, etc to allow a person to develop an understanding of how their foot placement measurements can vary with the various running/walking parameters. For example, the person may be able to determine from the displayed information that their foot overpronation becomes excessive at certain running speeds, such as due to a longer stride step distance, and can therefore adapt their running speed or allowed duration at that speed when running/walking on some types of surfaces based on that information. The person may alternatively or additionally determine from the displayed information that overpronation/supination is excessive during a warm-up phase of running, such as due to insufficient stretching, or near the end of a run, such as due to fatigue, and may thereby adapt their warm-up phase or end-run phase (e.g., select a softer running surface, run at a speed/stride distance) to reduce the excessive overpronation/supination.

Figure 2:
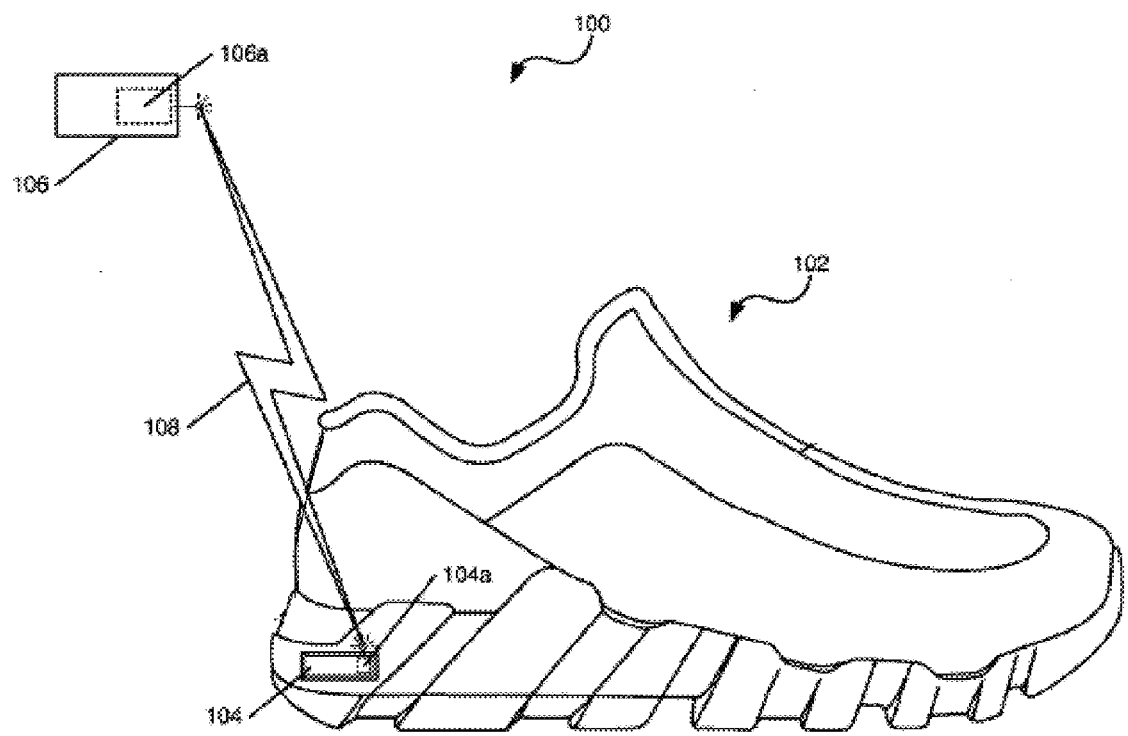
FIG. 2 illustrates an example impact measurement circuit that is within a shoe and wirelessly communicates to an impact alert circuit according to some embodiments of the present invention.

FIG. 2 illustrates an example impact measurement circuit 104 that is connected to a shoe 102 and wirelessly communicates impact measurements to an impact alert circuit 106 according to some embodiments of the present invention. The impact measurement circuit 104 is configured to measure impact from the shoe 102 striking a surface while a person is walking/running and/or to determine an angle of the leg/foot when the foot impacts the surface.

The impact measurement circuit 104 may include an accelerometer that is configured to measure impact from the foot striking the surface while the person is walking/running. Alternatively or additionally, the impact measurement circuit 104 may include a force transducer that is configured to measure force from the foot striking the surface while the person is walking/running. The force transducer may, for example, be configured to output a signal that indicates a measurement of the force, strain, and/or pressure in the material of the shoe sole (e.g., rubber sole) as the material compresses/expands responsive to the shoe impacting a surface. The impact measurement circuit 104 may be configured to generate a signal that indicates a peak magnitude of the measured impact.

The impact measurement circuit 104 may additionally or alternative include a tilt sensor that measures angle/tilt of the shoe/foot/leg when the shoe 102 impacts a surface, and may communicate the measured angle/tilt to the impact alert circuit 106 for use in determining foot positioning relative to the body at impact. The tilt sensor may include, but is not limited to, a multi-axis accelerometer, a multi-axis force transducer, mechanical movement device (e.g., rolling ball with position sensors), or other inclinometer or sensor. The impact measurement circuit may include one multi-axis sensor or may include spaced apart single-axis or multi-axis impact sensors (e.g., spaced apart in the direction of forward movement of the shoe) that can measure the back-to-front or front-to-back progression of the impact as the foot impacts a surface and rolls forward/backward.

The impact measurement circuit 104 may reside in one or more discrete packages that are, for example, connected to the shoe 102, and/or it may include a plurality of sensor elements that are spaced apart on the shoe to, for example, measure characteristics of the impact as the shoe rolls forward after impacting a surface and/or to measure characteristics of the impact as the shoe rolls inward/outward (e.g., due to pronation/supination) after impacting the surface. Accordingly, impact sensors may be spaced apart at locations in a heel portion and midfoot/forefoot location of the shoe, and/or impact sensors may be spaced apart at locations in a right and left portion of the shoe.

The impact measurement circuit 104 includes a transmitter circuit 104a that transmits the measured impacts to the impact alert circuit 106, which includes a receiver circuit 106a to receive the measurements. The measurements may be transmitted through a wireless air interface using one or more wireless protocols, such as, without limitation, Bluetooth, near field communication (NFC), WIFI (e.g., IEEE 802.11). The impact measurement circuit may be configured to be mounted/connected/embedded within a heel (rear) region of the person's shoe to increase sensitivity of the impact measurement from the foot striking a surface while the person is walking/running. Although the impact measurement circuit 104 is illustrated in FIG. 2 as being within a heel region of the shoe, the invention is not limited thereto because the impact measurement circuit 104 may reside in a mid-foot region or forefoot region of the shoe 102 or may be connected elsewhere on a person's body. For example, the impact measurement circuit 104 may be configured to be connected a person's ankle or leg (e.g., via a strap) or elsewhere that will provide sufficient sensitivity to changes in foot impact levels (e.g., impact magnitude), such as on a person's head or central body to sense accelerations/vibration transferred from the feet through a person's spine.

The impact alert circuit 106 is configured to notify the person as to how hard/soft the person's foot is impacting a surface, how much cushioning life remains in shoes, whether/how much the foot is impacting the surface relative to a preferable location relative to the body, and/or provide other information regarding foot placement on the surface, such as whether/how much the foot is impacting the surface at a rear-foot location, mid-foot location, forefoot location and/or whether/how much the foot is impacting the surface tilted to the right of left at impact.

Figure 3:
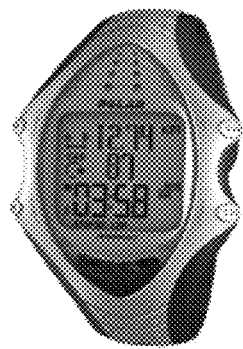
FIG. 3 illustrates a wrist watch that is configured to inform a person of characteristics of their foot impacting a surface while running/walking according to some embodiments of the present invention.
Figure 4:
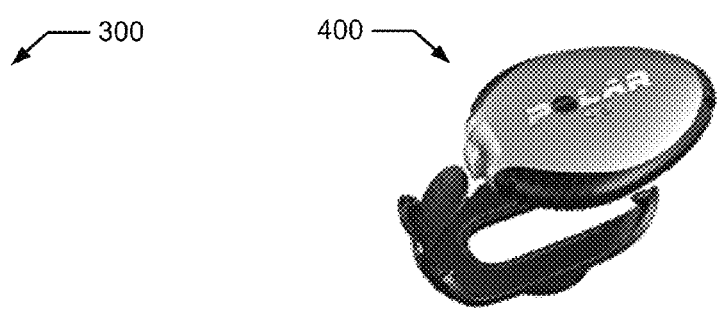
FIG. 4 illustrates an example impact measurement circuit that can be connected to a shoe and configured measure foot impact levels as a person is running/walking according to some embodiments of the present invention.
Figure 5:
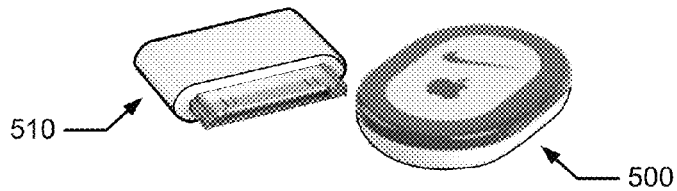
FIG. 5 illustrates another example impact measurement circuit configured according to some embodiments of the present invention.

FIGS. 3-5 illustrate various embodiments of impact measurement circuits and impact alert circuits that can be configured to operate as described herein. The invention is not limited to these example embodiments.

FIG. 3 illustrates a wrist watch 300 that includes an impact alert circuit that informs a person of characteristics of the foot impacting a surface while running/walking according to some embodiments of the present invention. The wrist watch 300 includes an informational display device that is configured to provide coaching to a runner/walker, such as by generating one or more of the information indicia of FIG. 1 or other indicia according to some embodiments of the present invention. The wrist watch 300 may include a sound generation device that is configured to generate sound to the person that audibly indicates a level of impact (e.g., an average level of impact or peak magnitude of impact) that is occurring when one/both of the person's feet are striking a surface.

FIG. 4 illustrates an example impact measurement circuit 400 that can be connected to a shoe (e.g., to the laces) to measure foot impact levels as a person is running/walking, and to transmit the measurements to a separate impact alert circuit (e.g., the watch 300 of FIG. 3) and/or to locally stored the measurements in a log file that can be later downloaded to an impact alert circuit (e.g., a personal computer, etc.). The log file may include individual impact measurements and/or an may store one or more accumulated impact metric that are generated by algorithmically combining (e.g., averaging, weighted averaging, arithmetic mean, geometric mean, harmonic mean, median, trending, etc.) individual impact measurements to generate an accumulated impact metric.

FIG. 5 illustrates another example impact measurement circuit 500 that can be connected to a shoe to measure a foot impact levels of person is running/walking, and to transmit the measurements to a receiver device 510 that is communicatively connected to a separate impact alert circuit. The impact measurement circuit 500 may be placed within the shoe, such as within or below a running pad in a heel region of the shoe (e.g., as shown in FIG. 2).

Figure 6:
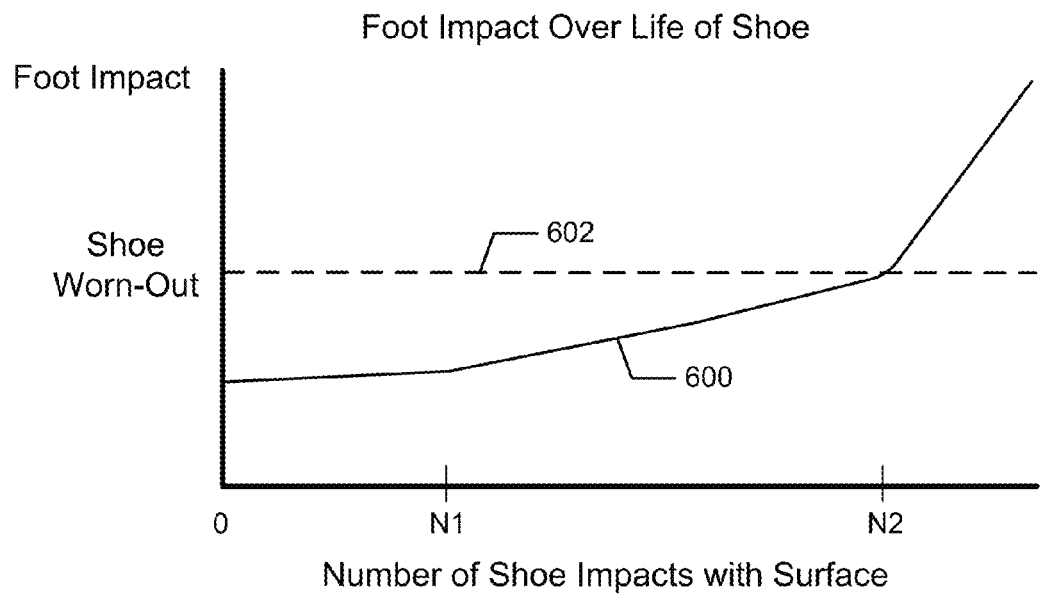
FIG. 6 is a graph that illustrates how the average impacts exerted on a foot while running/walking can substantially increase over the lifetime of a running shoe.

FIG. 6 is a graph 600 that illustrates how the average impact exerted on a foot while running/walking can substantially increase over the lifetime of a running shoe, represented by the number of surface impacts on the shoe. Referring to FIG. 6, a new shoe generally provides the greatest relative cushioning as the insole (which may be a removable pad on which the foot rests) and the thick midsole (e.g., layer of rubber or other supportive materials) function to cushion the feet by reducing the peak magnitude of the impacts between the shoe and surfaces as a person runs/walks. However, as the number of impacts increases (e.g., more than N1) the insole wears-out by failing to provide much impact cushioning relative to when the shoe was new (e.g., low relative use). As the number of impacts increases (e.g., between N1 and N2), the thick midsole continues to cushion the feet by reducing the peak impact magnitudes, however the level of cushioning gradually decreases with a corresponding increase in the impact magnitude experienced by the feet (e.g., illustrated by the first rate of increasing impact magnitude). In contrast, when the thick midsole wears-out (e.g., as the impacts approach N2), the shoe no longer provides sufficient impact cushioning for the feet and the peak impact magnitudes rapidly increase with continued use of the shoe, illustrated by the much greater second rate of increase of impact magnitude after N2 impacts with the average impacts exceeding a "worn-out" threshold 602. Continued use of the shoe for running or other higher impact activities may result in one or more of the above-described injuries due to much higher impact forces and/or vibrations traveling through the feet, legs, and body of the person. Accordingly, the trend of the impact levels over time or the rate of change in the trend can be used by the impact monitoring system to determine how much cushioning life remains in a pair of shoes.

In accordance with some embodiments, the foot impact monitoring system is configured to respond to a calibration signal from a person (e.g., by a person entering a command to calibrate the system for a new or different pair of shoes) by generating a baseline threshold level in response to an average of measurements of the levels of impact. Thus, the system may generate a baseline threshold level of the impact measurements while the shoes are providing good cushioning (e.g., between 0 and N1 in FIG. 6). The system can further generate an indication of how much shoe life remains (e.g., the shoe life indication 50 in FIG. 1) in response to the measured levels of impact over a defined number of impacts and the baseline threshold level. The system may alternatively or additionally display a warning on a display device and/or generate an audible warning when the shoe is determined to have become worn-out based on how much the monitored acceleration measurements have changed relative to the baseline threshold level. Accordingly, the system can inform a person how much cushioning life remains in a shoe and/or notify the person when the shoe no longer provides an acceptable level of cushioning by comparing the presently measured impacts to the baseline threshold level.

Alternatively or additionally, the system may generate an indication of how much shoe life remains and/or notify a person that a shoe has become worn-out in response to determining that the rate of change in the measured impacts has increased more than a threshold amount. For example, when the system determines that the rate of change in the peak magnitude of the impacts has increased from an average rate between N1 and N2 to a greater rate of change after N2, the system can determine therefrom that the shoe no longer provides sufficient impact cushioning for the feet and the peak impact magnitudes rapidly increase with continued use of the shoe.

Figure 7:
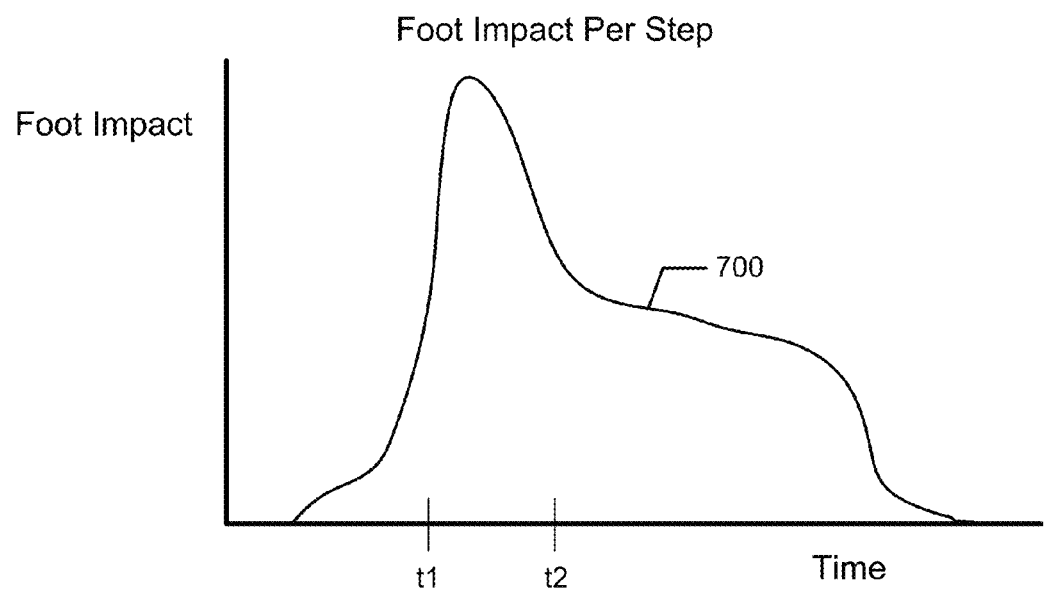
FIG. 7 is a graph that illustrates a single impact experienced by a foot relative to time from the foot striking a surface while a person is running.

FIG. 7 is a graph 700 that illustrates an example curve/trend in impact measurements during a single impact experienced by a foot relative to time from the foot striking a surface while a person is running. The impact force and acceleration rapidly increases from when the shoe initially impacts a surface (e.g., with a heel strike) to a peak magnitude, between time T1 and T2, as the sole of the shoe rapidly compresses to absorb some of the impact. The foot impact then more gradually decreases from the peak magnitude as the foot rolls forward (e.g., from a heel strike to mid-foot and then forefoot) compressing other regions of the sole of the shoe, and then the foot leaves the ground to be positioned for the next impact while the person is running/walking. In some embodiments, the impact alert circuit is configured to generate an indication to the person of a foot impact level in response to a peak magnitude of the measured impact, which may be particularly important information for the person to know in order to be able to adapt how the person is running/walking to avoid injury (e.g., by reducing the peak impact magnitude by stepping softer, impact the feet more under the body instead of in-front of the body, etc.).

The impact alert circuit may compare a magnitude, average, or other measurement associated with the peak pulse segment (e.g., between T1 and T2) to a magnitude, average, or other measurement of another segment of the impact (e.g., outside of the peak pulse (e.g., from T2 to the end of the measured impact) or inclusive of the peak pulse) to generate information that is used to regulate notifications of the impact level experienced when the foot impacts a surface. Because the measured impact level will vary with weight of the runner, comparison of peak pulse segment to the entire impact waveform or another segment outside of the peak pulse segment may enable the impact alert circuit to at least partially remove bias that is introduced into the measurements due to the person's weight. The impact alert circuit may, for example, be configured to respond to increase in the difference from the comparison by indicating to the person that the foot impact has increased, and conversely may respond to a decrease in the difference from the comparison by indicating to the person that the foot impact has decreased. The impact alert circuit may alternatively or additionally be configured to respond to an the difference from the comparison exceeding one or more defined thresholds by generating an excessive foot impact warning sound and/or displayed indicia (graphical or textual indication on a display device) indicating to the person that the foot impact has become excessive.

FIG. 7 may alternatively or additionally represent the level of impact or stress experience by a foot that impacting a surface and then rolling inward/outward due to excessive overpronation/supination. In some embodiments, the impact measurement circuit is configured to measure the sideways rolling impact for use by the impact alert circuit. The impact measurement circuit may include one multi-axis sensor or may include spaced apart single-axis or multi-axis impact sensors that can measure the sideways progression of the impact as the foot impacts a surface and rolls sideways. The impact alert circuit is configured to generate an indication for the person of whether and/or how much overpronation/supination is occurring based on the peak magnitude of the measured impact, based on the sideways acceleration, or other characteristics that reflect the rolling movement of the shoe due to overpronation/supination.

When used for monitoring sideways rolling movement (overpronation/supination), the impact alert circuit may compare a magnitude, average, or other measurement associated with the peak pulse segment (e.g., between T1 and T2) to a magnitude, average, or other measurement of another segment of the impact (e.g., outside of the peak pulse (e.g., from T2 to the end of the measured impact) or inclusive of the peak pulse) to generate information that is used to regulate notifications of the level of overpronation/supination experienced when the foot impacts a surface. Because the curve/trend in the measured impact levels will vary with weight of the runner, comparison of peak pulse segment to the entire impact waveform or another segment outside of the peak pulse segment may enable the impact alert circuit to at least partially remove bias that is introduced into the measurements due to the person's weight. The impact alert circuit may, for example, be configured to respond to an increase in the difference from the comparison by indicating to the person that the foot overpronation/supination has increased, and conversely may respond to a decrease in the difference from the comparison by indicating to the person that the foot overpronation/supination has decreased. The impact alert circuit may alternatively or additionally be configured to respond to an the difference from the comparison exceeding one or more defined thresholds by generating an excessive foot overpronation/supination warning sound and/or displayed indicia (graphical or textual indication on a display device) indicating to the person that the foot overpronation/supination has become excessive.

Figure 8:
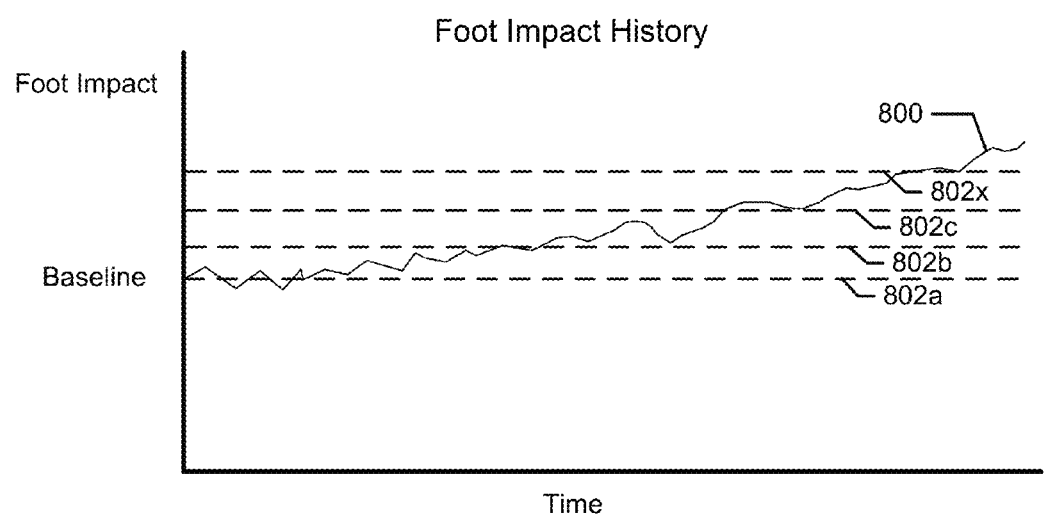
FIG. 8 is a graph that illustrates how the level of impact experienced by a foot while running can vary with hardness of the running surface, the speed of the runner, and fatigue of the runner.

FIG. 8 is a graph that illustrates how the level of impact 800 experienced by a foot while running can vary with hardness of the running surface, the speed of the runner, and fatigue of the runner. In some embodiments, the foot impact monitoring system is configured to generate a baseline threshold level in response to an average of measurements of the levels of impact. The average may be made over an initial calibration timeframe (e.g., baseline level 802a), and/or may be a running average over a defined interval (e.g., more than one minute or, in some embodiments, more than ten minutes to filter out minor variations that occur while running/walking) to repetitively generate baseline levels (e.g., baseline levels 802b-x). The system may then generate an audible notification and/or display a visual notification that informs the person whether they are experiencing a higher or lower foot impact than the baseline threshold level. In some embodiments, the impact alert circuit is configured to graph the measured levels of impact relative to an elapsed time of the activity (e.g., to generate a foot impact graph, such as the example graph 800 of FIG. 8), and may further display the impact levels relative to a speed at which the person was walking/running and/or a distance that the person walked/ran. The person may thereby analyze whether excessive foot impact levels are occurring at certain running/walking speeds, occurring as a result of fatigue, occurring on certain sloped segments of a route taken by the person, and/or occurring on certain types of surfaces traversed by the person, and may respond by taking corrective actions.

Figure 9A:
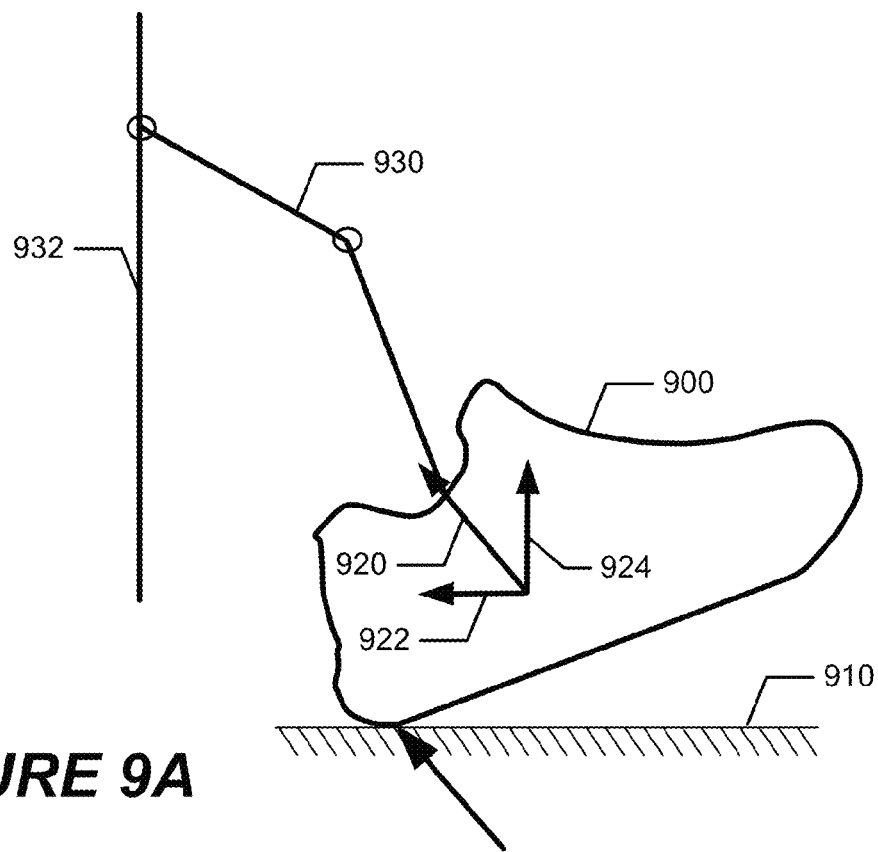
FIG. 9A illustrates using a side view of a shoe how improper foot placement too far ahead of the person's body while running/walking results can result in an unnecessary impact component force into the foot and leg and an unnecessary impact component force that retards forward movement of the runner/walker.

FIG. 9A illustrates what happens when a person runs/walks by improperly impacting a feet 900 with a surface 910 too far ahead of the person's body 932. Because the foot 900 is impacting too far ahead of the body 932, a resultant force 920 is created is angled backward from the direction of movement and has an undesirable horizontal force component 922 opposite to the direction of movement along with a vertical force component 924. The opposite horizontal force component 922 retards forward movement of the person and, coupled through the moment arm between the point of contact and the ankle/knee and hip, creates rotational moment forces that undesirably stress bones, tendons, and muscles in the foot, ankle, shin, knee, and hip.

In accordance with some embodiments, the impact alert circuit is further configured to determine from characteristics of the measured impact when the person is placing a foot 900 excessively forward when striking the surface 910 and resulting in excessive undesirable slowing forces exerted on the foot 900 and retarding forward movement of the person. The impact alert circuit can generate an audible/visual warning to the person that an improper foot placement condition exists responsive to the determination that the person is placing the foot excessively forward when striking the surface 910. The impact alert circuit may determine from acceleration, pressure, and/or force measurements by an impact measurements circuit when the angle of the impact force indicates that the foot 900 is striking the surface 910 too far ahead of the body 932, and can provide audible/visually guidance to the person as actions are taken changing the relative impact distance of the foot 900 from the body to reduce the horizontal force component 922 to an acceptable level. In some embodiments, the impact alert circuit is configured to use a measured horizontal and/or vertical component of the impact to determine where the feet are impact the surface relative to the body. In some other embodiments, the impact measurement circuit includes a tilt sensor that measures an angle of the leg/foot when the foot impacts the surface, and communicates the measured angle to the impact alert circuit for use in determining where the feet are impact the surface relative to the body or another reference location. The impact measurement circuit may compare an impact measurement in a rear portion of the shoe to an impact measurement in forward portion of the shoe to generate an indication of whether and to what extent the shoe is impacting heel first, midfoot first, or toe first, and can generate an audible sound and/or display a graphical/textual indication to the person of a result of the analysis.

For example, with reference to FIG. 1, the impact alert circuit may generate the foot placement coach display 40 and regulate distance between the displayed marker 44, which represents a present location of where the foot 900 is striking the surface 910 relative to an ideal impact location (e.g., location 932). When the backward horizontal force component 922 and/or angle of impact decreases, the impact alert circuit may display the marker 44 closer to the ideal impact location (vertical line in display 40). Conversely, the impact alert circuit may display the marker 44 further ahead of the ideal impact location responsive to measurement of an increasing backward horizontal force component 922 and/or greater angle at impact. The ideal impact location may be calibrated to correspond to a location near the person's body that reduces backward horizontal force component 922 against the foot 900 and/or provides a desired foot strike location on the foot 900 (e.g., rear foot, midfoot, forefoot strike location). When the foot impact monitoring system is carried by the person while running/walking, the person may dynamically view the foot placement informational display 40 and make adjustments with where the foot 900 is striking the surface 910 to avoid unnecessary impact forces/vibration on person's muscular, tendon, and skeletal structure of the feet, legs, and body.

In some other embodiments, the impact measurement circuit can include a tilt sensor that measures an angle of the shoe 900 relative to the direction of movement (i.e., frontward/backward angle) when the shoe 900 impacts the surface 910, and communicates the measured angle to the impact alert circuit for use in determining whether and/or how much the foot is impacting the surface at a rear-foot location, mid-foot location, forefoot location. For example, when the impact measurement circuit determines that the shoe 900 is impacting the surface 910 angled significantly upward (e.g., relative to one or more threshold angle values), the impact alert circuit may respond thereto by generating an audible notification (e.g., tone) and/or visual notification (e.g., display text/graphical object) to the person that the person is running/walking with an excessive rear-foot heel strike angle. Alternatively, when the impact measurement circuit determines that the shoe 900 is impacting the surface 910 angled relatively flat (e.g., relative to one or more threshold angle values), the impact alert circuit may respond thereto by generating an audible notification (e.g., tone) and/or visual notification (e.g., display text/graphical object) to the person that the person is running/walking with an a mid-foot (e.g., flat foot) strike angle. Similarly, when the impact measurement circuit determines that the shoe 900 is impacting the surface 910 angled relatively downward (e.g., relative to one or more threshold angle values), the impact alert circuit may respond thereto by generating an audible notification (e.g., tone) and/or visual notification (e.g., display text/graphical object) to the person that the person is running/walking with a forefoot (e.g., toe) strike angle.

Running with a heel foot strike, if excessive, may aggravate the calf muscles and Achilles tendon and contribute to overstriding, slower running, and poorer form. Midfoot strike may provide better impact absorption due to a bent-leg, and provide less stress on the calf muscles and Achilles tendon. Toe strike may provide less stress on the knees and ankles and provide faster running form, however it may also contribute to shin splints, Achilles tendinitis and muscle pulls from maintaining the calf muscle contracted. The present notification may enable a person to dynamically adjust the foot placement with quantitative feedback from the impact alert circuit.

The impact measurement circuit may combine impact measurements with impact measurements to determine whether the impact angle indicates that this particular person is running/walking with an undesirable form (e.g., injury prone or energy wasteful form). For example, when the measurements indicate that the shoe 900 is impacting the surface 910 with a downward angle and the impact has a threshold rearward component, the impact measurement circuit may notify the person that the shoe 900 is being dragged forward, which not only wastes energy while running, but which also may create unnecessary stress on the lower leg and be prone to leading to a fall if the shoe 900 catches a rock/crack/etc on the surface 910.

Figure 9B:
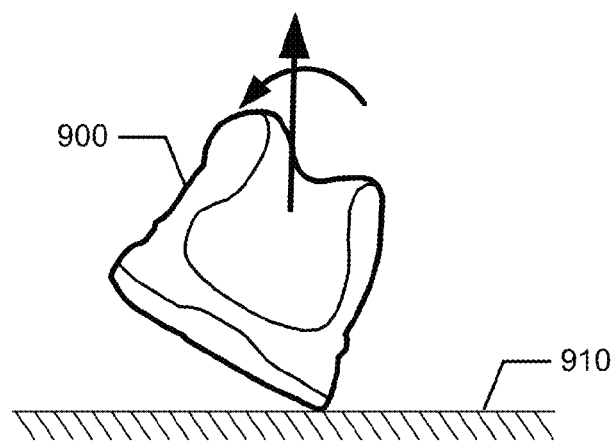
FIG. 9B illustrates using a rear view of a shoe how improper foot placement at an angle causing overpronation or supination while running/walking results can result in undesirable rotational forces on the foot and leg.

FIG. 9B illustrates how improper foot placement at an angle causing overpronation or, alternatively, supination while running/walking results can result in undesirable rotational forces on the foot and leg. In some other embodiments, the impact measurement circuit can include a tilt sensor that measures an angle and/or rolling movement of the shoe 900 side-to-side (i.e., angled toward right/left) when the shoe 900 impacts the surface 910, and communicates the measured angle and/or movement to the impact alert circuit for use in determining whether and/or how much the foot tilted toward the right/left when impacting the surface 910 (e.g., whether and/or how much the foot is impacting with overpronation, normal pronation, or supination). The impact measurement circuit may generate an audible notification (e.g., tone) and/or visual notification (e.g., display text/graphical object) to the person that indicates whether the shoe 900 is impacting with an undesirable angle, and may provide an indication of whether the shoe is moving through an overpronation, normal pronation, or underpronation cycle upon impact, and may provide a further indication of how far the shoe 900 is overpronating or underpronating (e.g., using the overpronation/ supination graph 46-49 of FIG. 1 or another graphical or textual indication of the measured condition). This notification may enable a person to actively adjust the foot placement, such as in real-time, (e.g., by running with feet closer together or further apart, increasing or decreasing the step stride, and/ or regulating the allowed angle of the ankle-foot by conscious control of ankle muscles) to improve the motion of the feet and avoid stress and related injuries that can result when improperly angled feet are forced to roll inward/outward with each surface impact.

Figure 10:
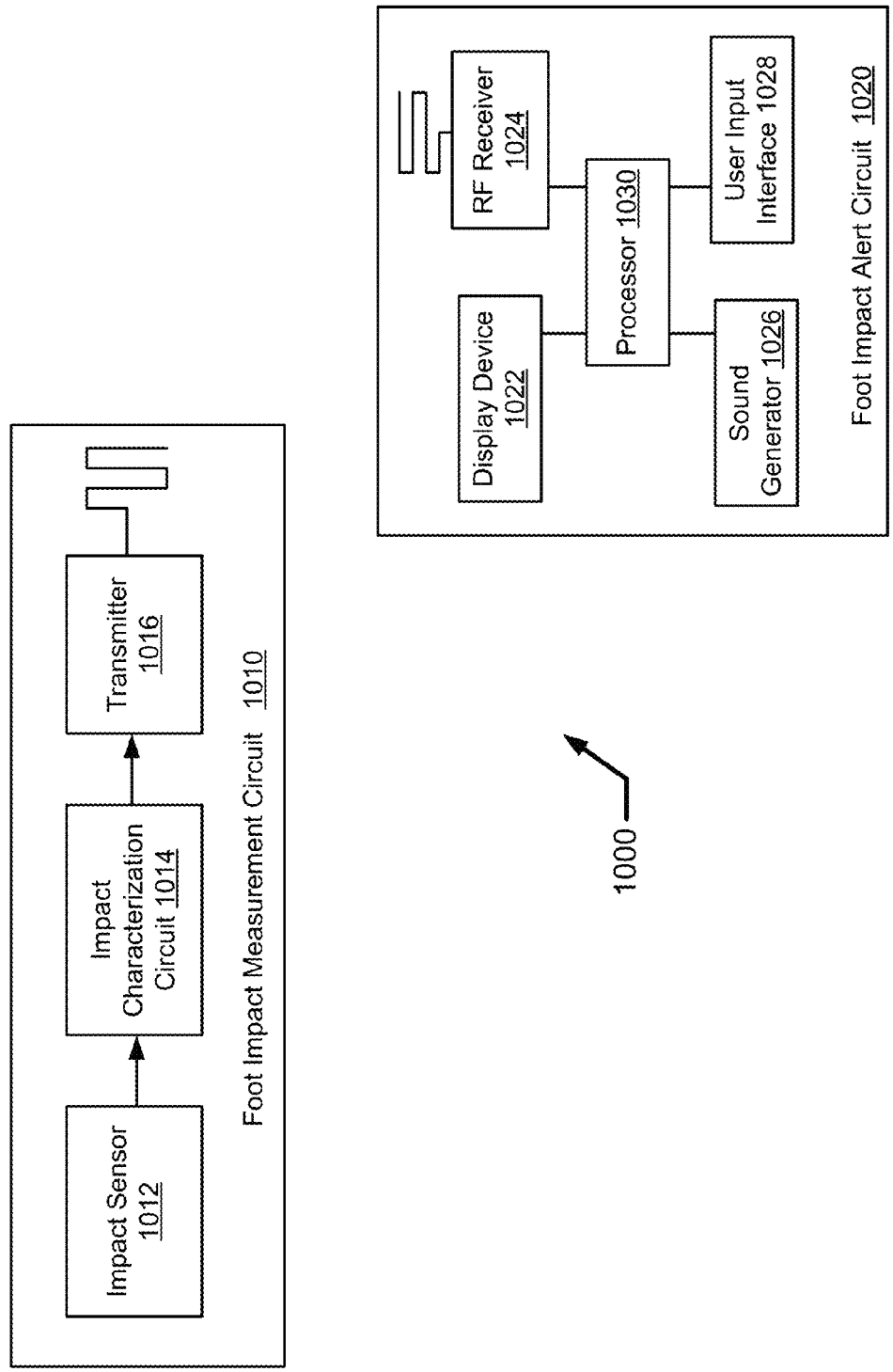
FIG. 10 is a block diagram of a foot impact monitoring system according to some embodiments of the present invention.

FIG. 10 is a block diagram of a foot impact monitoring system 1000 according to some embodiments of the present invention. The foot impact monitoring system 1000 includes a foot impact measurement circuit 1010 and a foot impact alert circuit 1020. The measurement circuit 1010 includes an impact sensor 1012, an impact characterization circuit 1014, and a transmitter 1016. The impact sensor 1012 may include an accelerometer that is configured to measure impact from the foot striking the surface while the person is walking/ running. Alternatively or additionally, the impact sensor 1012 may include a force transducer that is configured to measure force from the foot striking the surface while the person is walking/running. The force transducer may, for example, be configured to output a signal that indicates a measurement of the force, strain, and/or pressure in the material of the shoe sole (e.g., rubber sole) as the material flexes responsive to the shoe impacting a surface. The impact measurement circuit 1010 may be configured to generate a signal that indicates a peak magnitude of the measured impact.

The impact measurement circuit 106 may include a tilt sensor that measures angle/tilt of the foot/leg when the foot impacts a surface, and may communicate the measured angle/ tilt to the impact alert circuit 1020 for use in determining foot positioning relative to the body at impact. The tilt sensor may include, but is not limited to, a multi-axis accelerometer, a multi-axis force transducer, mechanical movement device (e.g., rolling ball with position sensors), or other inclinometer or sensor.

The impact measurement circuit 106 may include a piezoelectric transducer, potentiometric (e.g., spring-mass system), reluctive (e.g., inductive bridge), strain gauge, and/or capacitive device that outputs a signal that indicates a level of the measured impact.

The impact characterization circuit 1014, which is optional, may filter the signal from the impact sensor 1012 to generate a signal appropriate for transmission, and may covert the signal from an analog signal to a digital representation that can be transmitted as a digital signal through the transmitter 1016 and a wireless interface to the foot impact alert circuit 1020. The impact characterization circuit 1014 may average or otherwise combine the output signal from impact sensor 1012 over to a defined time interval to output a signal for transmission via the transmitter 1016. The transmitter 1016 may use one or more wireless protocols, such as, without limitation, Bluetooth, near field communication (NFC), WIFI (e.g., 802.11), to transmit the measured impact to the alert circuit 1020.

The foot impact alert circuit 1020 may include a display device 1022, a RF receiver 1024, a sound generation device 1026, and a user input interface 1028 there are controlled by a processor 1030. The RF receiver 1024 is configured to receive the measured impact information from the foot impact measurement circuit 1010.

The display device 1022 is configured to display foot impact information, foot placement information, remaining shoe cushioning life information, and/or other information that can be useful to a person while the person is running/ walking and/or for review after completing the activity.

The sound generation device 1026 is configured to generate an audible signal that communicates foot impact information, foot placement information, remaining shoe cushioning life information, and/or other information that can be useful to a person while the person is running/walking and/or for review after completing the activity.

The user input interface 1028 is configured to receive commands from the user, such as a command to generate the baseline threshold level for a new or different pair of shoes, against which other measurements are compared to determine whether excessive foot impact occurring, improper foot placement is occurring, and/or to determine remaining shoe cushioning life.

The processor 1030 may include one or more data processing circuits, such as a general purpose and/or special purpose processor (e.g., microprocessor and/or digital signal processor). The processor 1030 is configured to execute computer program instructions from memory circuitry/devices, described herein as a computer readable medium, to perform some or all of the operations and methods that are described herein for one or more of the embodiments disclosed herein. Accordingly, the processor 1030 can be configured by execution of the computer program instructions to carry out at least some of the functionality described herein respond to the impact measurements by generating for a person an indication of how much impact occurred from a foot striking a surface, and other functionality described herein.

Although the foot impact measurement circuit 1010 and the foot impact alert circuit 1020 have been shown as being separate devices that communicate through a wireless interface, the invention is not limited thereto. In some embodiments, the foot impact measurement circuit 1010 and the foot impact alert circuit 1020 may be combined within a single physical device package, or some of the functionality described herein may be combined into a single physical device package. For example, some or all of the analysis of the impact measurements by the impact sensor 1012 described herein may be carried out within the foot impact measurement circuit 1010, such within the impact characterization circuit 1014, and the output of the analysis may then be communicated to the foot impact alert circuit 1020 for display on the display device 1022 and/or to control the sound generator 1026 to output notifications to the person. Alternatively, the impact measurement analysis, the display functionality, and/or the sound generation functionality described herein for analyzing or notifying a person may be carried out within the same physical package, and which may be attached to the shoe, ankle, leg, head, or elsewhere on the person where the desired functionality can be performed.

Figure 11:
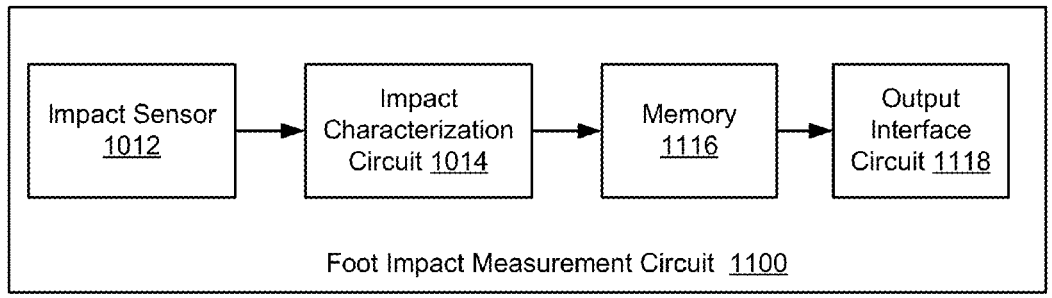
FIG. 11 is a block diagram of a foot impact measurement circuit that logs foot impact measurements according to some embodiments of the present invention.

FIG. 11 is a block diagram of another embodiment of a foot impact measurement circuit 1100 that logs foot impact measurements according to some embodiments of the present invention. The measurement circuit 1100 may include the impact sensor 1012 and the characterization circuit 1014 of FIG. 10. However, in contrast to the measurement circuit 1010 of FIG. 10, the measurement circuit 1100 of FIG. 11 is configured to locally store the impact measurements in a memory 1116 as a measurement log, instead of transmitting them in real-time to a foot impact alert circuit. Accordingly, after the person has completed an activity, the measurement log can be downloaded from the memory 1116 through an output interface circuit 1118 (e.g., a USB interface or other serial/parallel wired/wireless interface) to a foot impact alert circuit.

Figure 12:
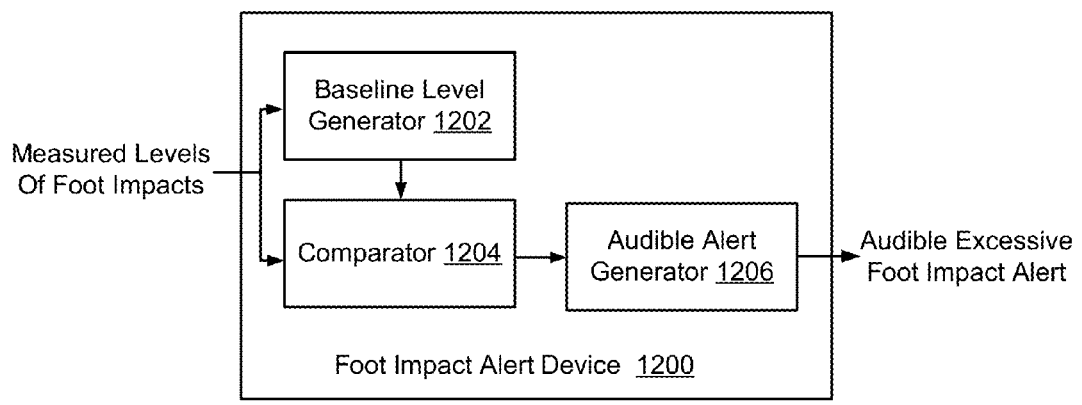
FIG. 12 is a block diagram of a foot impact alert circuit that generates audible foot impact notifications according to some embodiments of the present invention.

FIG. 12 is a block diagram of another embodiment of a foot impact alert circuit 1100 that generates audible foot impact notifications according to some embodiments of the present invention. The alert circuit 1200 can include a baseline level generator 1202, comparator 1204, an audible alert generator 1206. The baseline level generator 1202 is configured to generate a baseline threshold level in response to an average of measurements of the levels of impact, which are received from a foot impact measurement circuit. The baseline level generator 1202 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1202 may generate the baseline threshold level as a running average over a defined interval.

The comparator 1204 may compare measured levels of foot impact to the baseline threshold level and cause the audible alert generator 1206 to generate an audible foot impact warning sound that informs the person whether he/she is experiencing a higher or lower foot impact than the baseline threshold level (e.g., when the measured levels of impact exceed the baseline threshold level).

Accordingly, using the foot impact alert circuit 1200 of FIG. 12, the person can be audibly warned when the person's feet are impacting the surface at levels that exceed a baseline threshold level. The person may cause calibration of the baseline threshold level while the person is running with a pair of shoes having a desired level of cushioning and/or while the person is running with a level of foot impact that the person finds to be in a acceptable level and/or an upper range of an acceptable level, above which the person wants the circuit 1200 to provide an audible warning so that the person can take action to reduce the impact levels.

Figure 13:
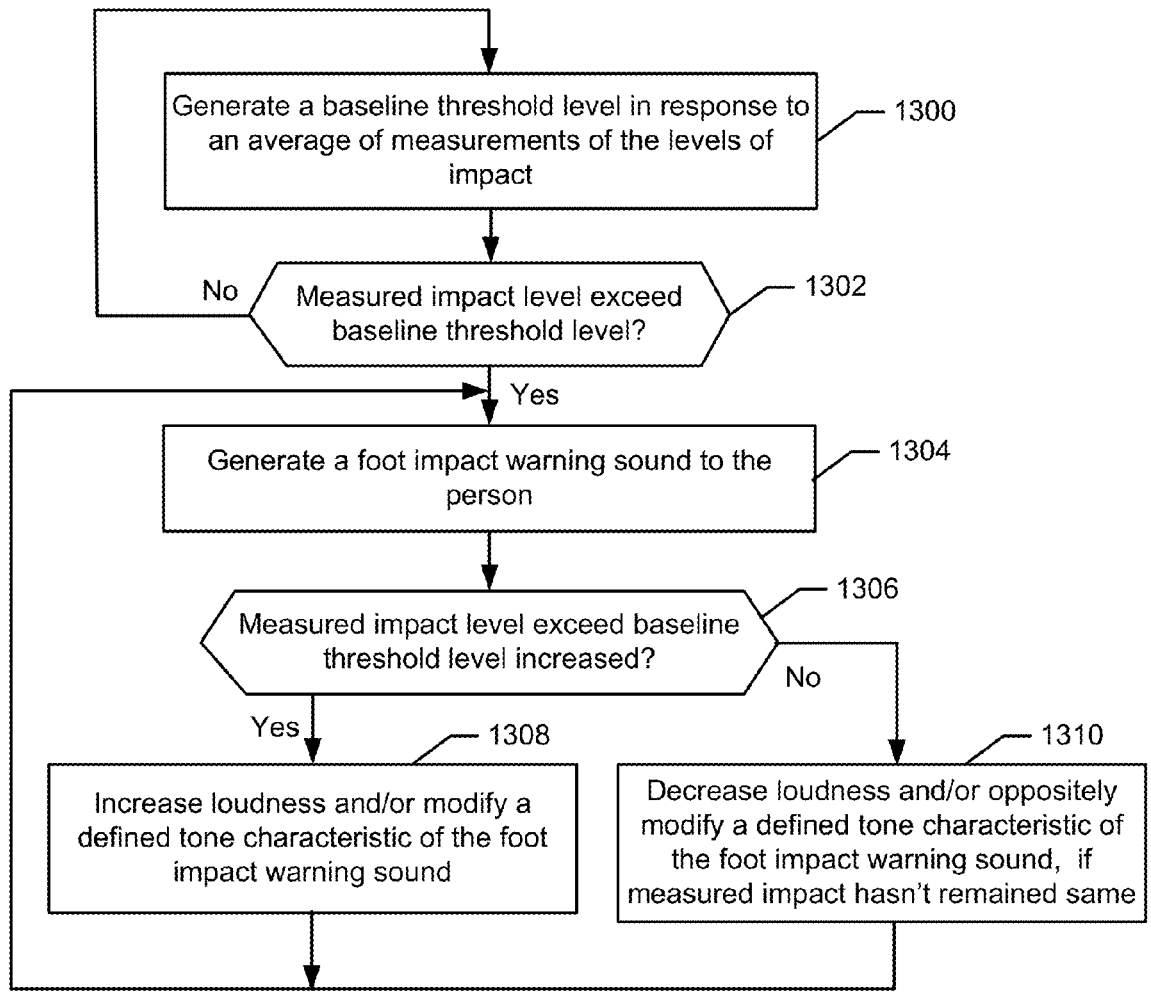
FIG. 13 is a flowchart of operations and methods for generating a foot impact warning sound to a person and regulates loudness and/or tone of the sound responsive to measured levels of foot impact while walking/running.

FIG. 13 is a flowchart of operations and methods for generating a foot impact warning sound to a person and regulates loudness and/or tone of the sound responsive to measured levels of foot impact while walking/running. Referring to FIG. 13, a foot impact alert circuit (e.g., alert circuit 1200) generates (block 1300) a baseline threshold level in response to an average of measurements of the levels of impact. A decision (block 1302) is made as to whether the measured impact level exceeds the baseline threshold level and, if so, a foot impact warning sound is generated (block 1304) to the person. The operations may include a further decision (block 1306) is made as to whether the measured impact level exceeds the baseline threshold level by an increasing or decreasing amount.

When the measured level of the impact exceeds the baseline threshold level by an increased amount, the impact alert circuit 1200 responds (block 1308) by increasing loudness and/or modifying a defined tone characteristic (e.g., increase/decrease frequency, pitch, etc.) of the foot impact warning sound generated by the sound generation device to audibly indicate to the person when the level of impact from the foot striking the surface has increased. In contrast, when the measured level of the impact exceeds the baseline threshold level by a decreased amount, the impact alert circuit 1200 responds (block 1310) by decreasing loudness and/or oppositely modifying the defined tone characteristic (e.g., decrease/increase frequency, pitch, etc.) of the foot impact warning sound generated by the sound generation device to audibly indicate to the person when the level of impact from the foot striking the surface has decreased. When the measure level of the impact has not changed relative to the baseline threshold level, the defined tone may be maintained as having the previous iteration characteristics.

Figure 14:
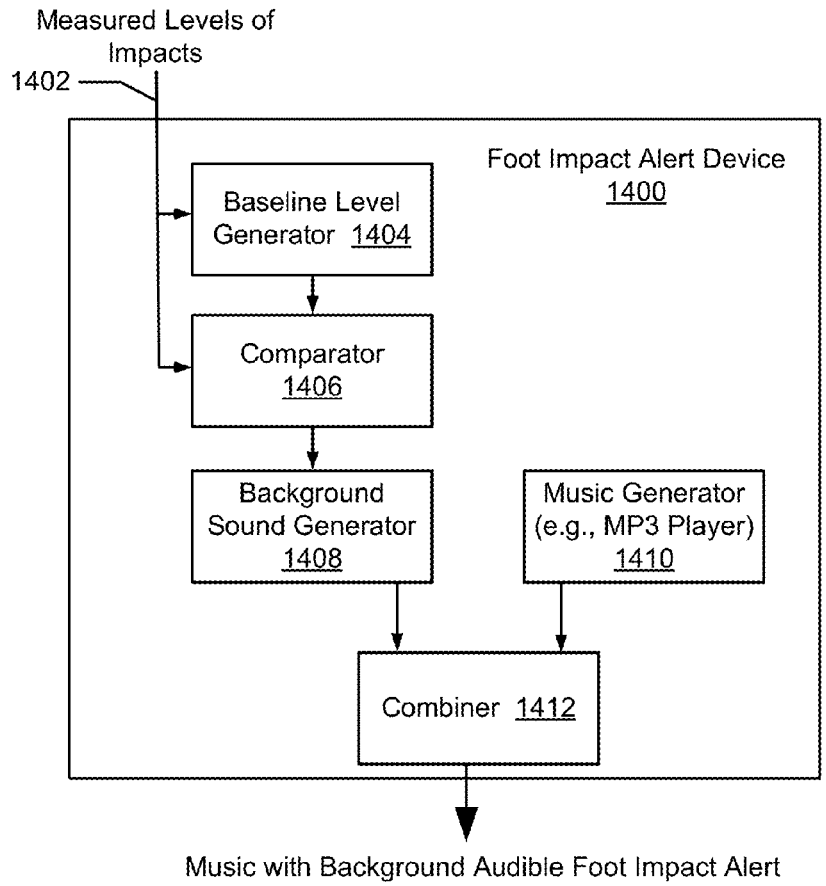
FIG. 14 is a block diagram of a foot impact alert circuit that is configured to combine background sound and music played through a music player to provide audible notification of measured foot impact levels while running/walking according to some embodiments of the present invention.
Figure 15:
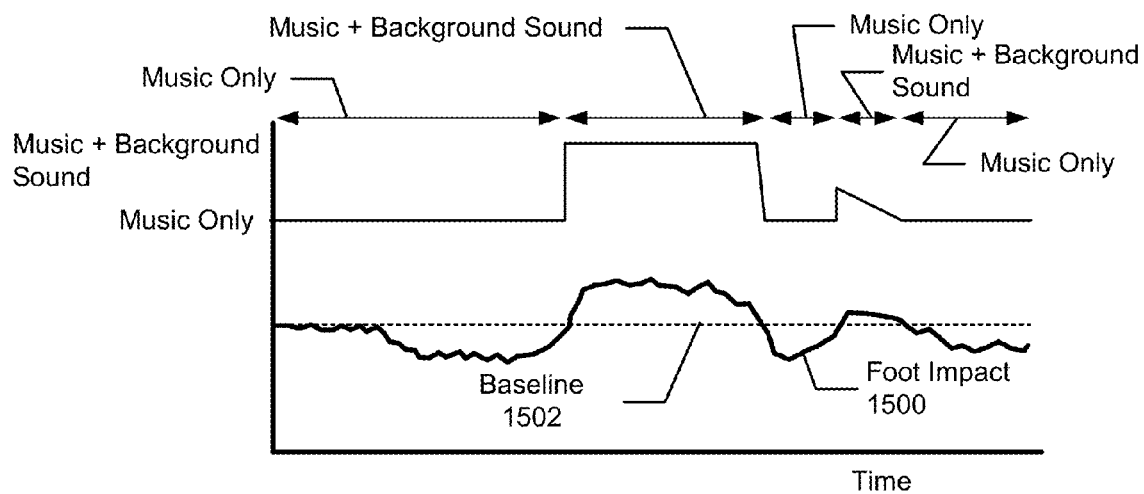
FIG. 15 illustrates graphs that show when only-music or a combination of music and background is played responsive to the measured foot impact levels according to some embodiments of the present invention.
Figure 16:
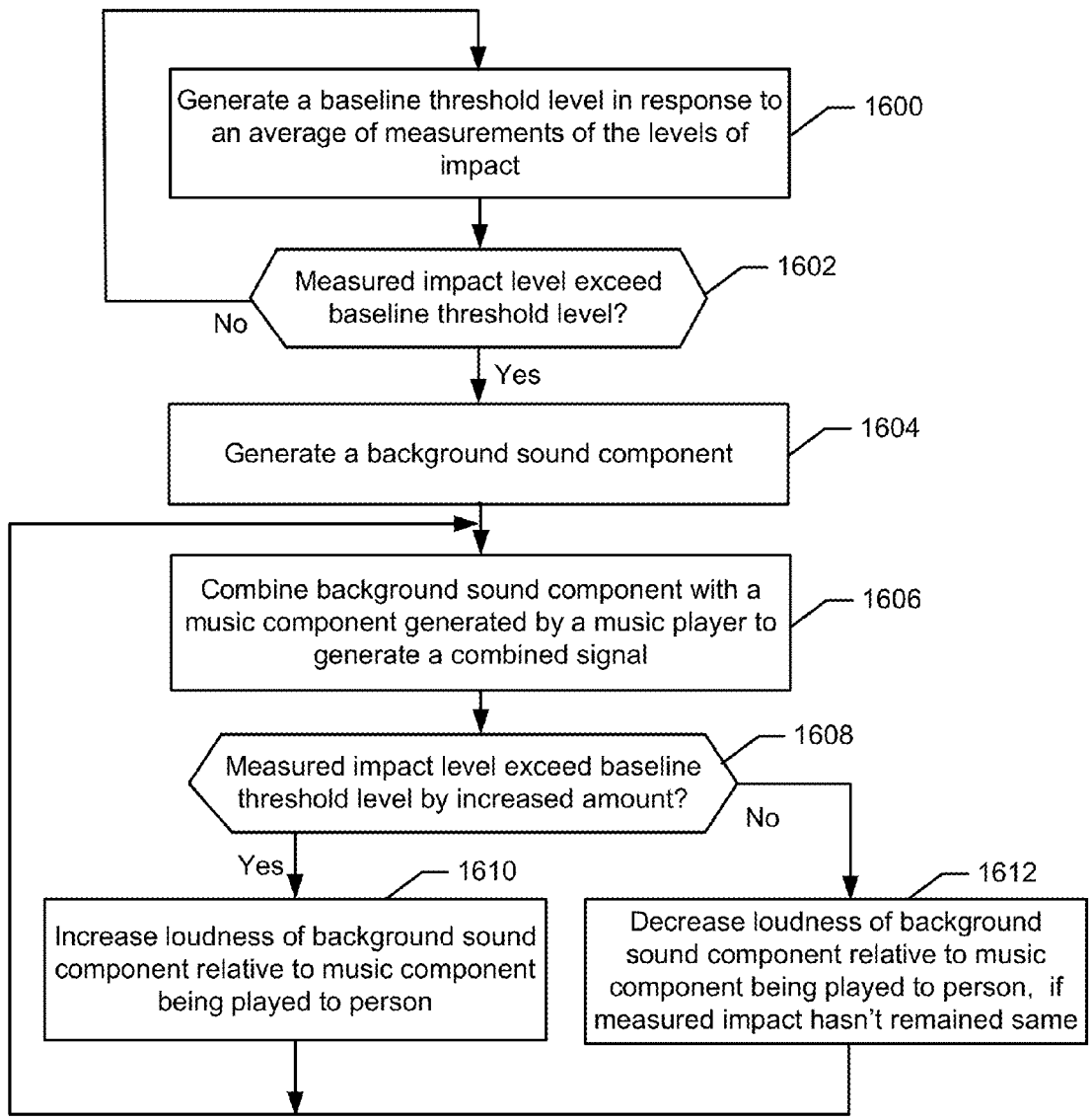
FIG. 16 is a flowchart of operations and methods that combine background sound and music played through a music player to provide audible notification of measured foot impact levels while running/walking according to some embodiments of the present invention.

FIG. 14 is a block diagram of a foot impact alert circuit 1400 that combines background sound and music played through a music player to provide audible notification of measured foot impact levels while a person is running/walking, according to some embodiments of the present invention. FIG. 15 illustrates graphs that show when only-music or a combination of music and background is played through a speaker to a person responsive to the measured foot impact levels, according to some embodiments of the present invention. FIG. 16 is a flowchart of operations and methods that combine background sound and music played through a music player to provide audible notification of measured foot impact levels while a person is running/walking, according to some embodiments of the present invention.

Referring to FIGS. 14-16, the foot impact alert circuit 1400 receives measurements 1402 of levels of foot impact from a foot impact measurement circuit. The foot impact alert circuit 1400 includes a baseline level generator 1404, the comparator 1406, the background sound generator 1408, a music generator 1410, and a combiner 1412.

The baseline level generator 1404 generates (block 1600 of FIG. 16) a baseline threshold level in response to an average of measurements 1402 of levels of foot impact. The generator 1404 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1404 may generate the baseline threshold level as a running average over a defined interval (e.g., over at least one minute to filter out minor variations that occur while running/walking).

The comparator 1406 may compare (block 1602 of FIG. 16) measurements 1402 of levels of foot impact to the baseline threshold level. The comparator 1406 may respond to a presently measured impact level exceeding the baseline threshold level by causing the background sound generator 1408 to generate (block 1604 of FIG. 16) a background sound component. The combiner 1412 combines (block 1606 of FIG. 16) the background sound component with a musical component, that is output by the music generator 1410, to generate a combined signal that is output to a person, via a speaker that may be within the alert circuit 1400 and/or connected thereto by the wired connection and/or wireless connection, to audibly indicate to the person how much impact occurred from the foot striking the surface.

The music generator 1410 may include, but is not limited to, a digital music player (e.g., a MP3/WMA/AIFF/or other digital format music player), a video player (e.g., MPEG, DVD, Blue-Ray, or other video player), a broadcast (terrestrial/satellite/internet/cable) radio receiver, and/or a broadcast (terrestrial/satellite/internet/cable) television/movie/video receiver.

Although some of the functional blocks of FIG. 14 have been illustrated as being separate blocks, they are not limited thereto because their functionality may be combined in fewer or greater numbers of functional elements. For example, some or all of the functional blocks of FIG. 14 may be combined into one device, such as the music generator 1410. In one embodiment, the combiner 1412 may be connected (e.g., as a two-input-one-output Y-connector) to an output of the music generator 1410 (e.g., a headset output jack output) to add the background sound component to the output of the music generator 1410, and the output of the combiner 1412 may be fed to headphones or another sound generation device.

The operations may include a further decision (block 1608) as to whether the measured impact level exceeds the baseline threshold level by an increasing or decreasing amount.

When the measured level of the impact exceeds the baseline threshold level by an increased amount, the impact alert circuit 1400 responds (block 1610) by increasing loudness of the background sound component relative to the music component of the combined signal being played to the person in response to a presently measured level of the impact exceeding the baseline threshold level by an increased amount to audibly indicate to the person when the level of impact from the foot striking the surface has increased. In contrast, when the measured level of the impact exceeds the baseline threshold level by a decreased amount, the impact alert circuit 1400 responds (block 1612) by decreasing loudness of the background sound component relative the music component of the combined signal being played to the person in response to a presently measured level of the impact exceeding the baseline threshold level by a decreased amount to audibly indicate to the person when the level of impact from the foot striking the surface has decreased. When the measure level of the impact has not changed relative to the baseline threshold level, the background sound component may be maintained at the previous iteration characteristics.

The background sound that is generated by the background sound generator 1408 may be any sound that can be identified by a user as in indication of the measured foot impacts. For example, the background sound may be a white noise (e.g., flat power spectral density) that can be added to the sound component to generate the combined signal that is played to the person. Alternatively or additionally, the background sound may be a repeating tone (e.g., a drum beat).

While a person is running, the background sound can controlled to be louder (e.g., a louder static noise sound combined with the music component) to indicate when the feet are impacting the surface harder, and can controlled to be quieter (e.g., a level static noise sound combined with the music component) to indicate when the feet are impacting the surface softer. Alternatively or additionally, the background sound can controlled to have an increased/decreased frequency and/or pitch (e.g., a faster tone beat and/or sharper tone combined with the music component) to indicate when the feet are impacting the surface harder, and can controlled to have a decreased/increased frequency and/or pitch (e.g., a slower tone beat and/or duller tone combined with the music component) to indicate when the feet are impacting the surface softer.

Reference is now made to the example graphs of FIG. 15 which show when only-music or a combination of music and background is played responsive to the measured foot impact levels according to some embodiments of the present invention. A graph of the measured foot impact levels 1500 are plotted relative to a baseline threshold level 1502. While the measured foot impact levels 1500 are less than the baseline 1502, the foot impact alert generator 1400 may respond by outputting from the combiner 1412 only the music component (e.g., no background sound component). In contrast, while the measured foot impact levels 1500 are greater than the baseline 1502, the foot impact alert generator 1400 may respond by outputting from the combiner 1412 a combined signal that includes the background sound component and the music component. The alert generator 1400 may further regulate the relative magnitude (e.g., loudness) of the background sound component relative to the music component in the output combined signal in responsive how much the measured foot impact levels 1500 exceed the baseline 1502.

Figure 17:
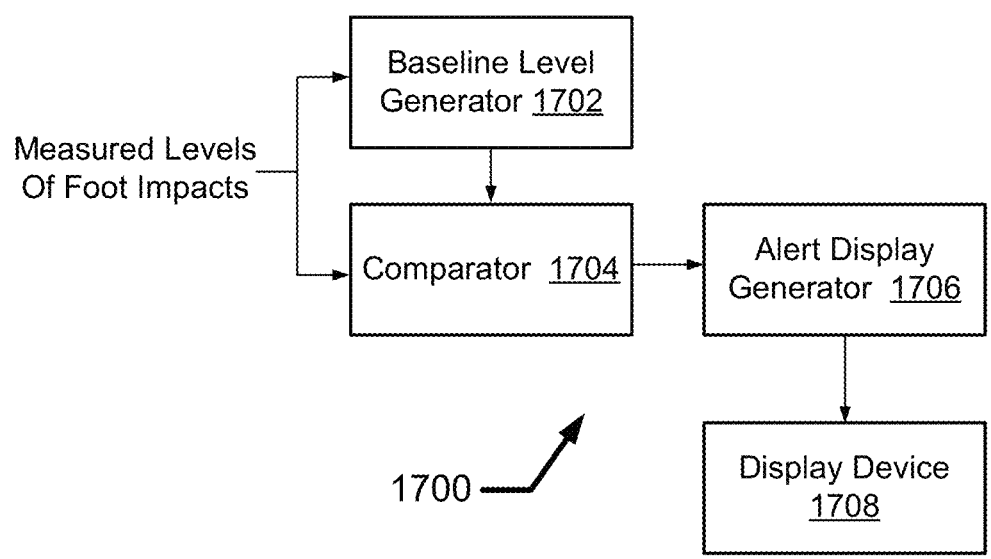
FIG. 17 is a block diagram of a foot impact alert circuit that generates visual indicia that notify a runner/walker of measured foot impact levels while running/walking according to some embodiments of the present invention.

FIG. 17 is a block diagram of a foot impact alert circuit 1700 that generates visual indicia that notify a runner/walker of measured foot impact levels while running/walking according to some embodiments of the present invention. The alert circuit 1700 can include a baseline level generator 1702, comparator 1704, an alert display generator 1706. The baseline level generator 1702 is configured to generate a baseline threshold level in response to an average of measurements of the levels of impact, which are received from a foot impact measurement circuit. The baseline level generator 1702 may respond to a calibration signal from a person (e.g., by a person entering a command to calibrate the system for a new or different pair of shoes) by generating a baseline threshold level in response to an average of measurements of the levels of impact. Alternatively or additionally, the baseline level generator 1702 may generate the baseline threshold level as a running average over a defined interval. The comparator 1704 may compare measured levels of foot impact to the baseline threshold level and cause the alert display generator 1706 to generate an foot impact warning indicia on the display device 1708 that informs the person whether they are experiencing a higher or lower foot impact than the baseline threshold level (e.g., when the measured levels of impact exceed the baseline threshold level).

Accordingly, using the foot impact alert circuit 1700 of FIG. 17, the person can be visually warned when the person's feet are impacting the surface at levels that exceed a baseline threshold level. The person may cause calibration of the baseline threshold level while the person is running with a pair of shoes having a desired level of cushioning and/or while the person is running with a level of foot impact that the person finds to be in a acceptable level and/or an upper range of an acceptable level, above which the person wants the circuit 1700 to display an visible warning so that the person can take action to reduce the impact levels.

Figure 18:
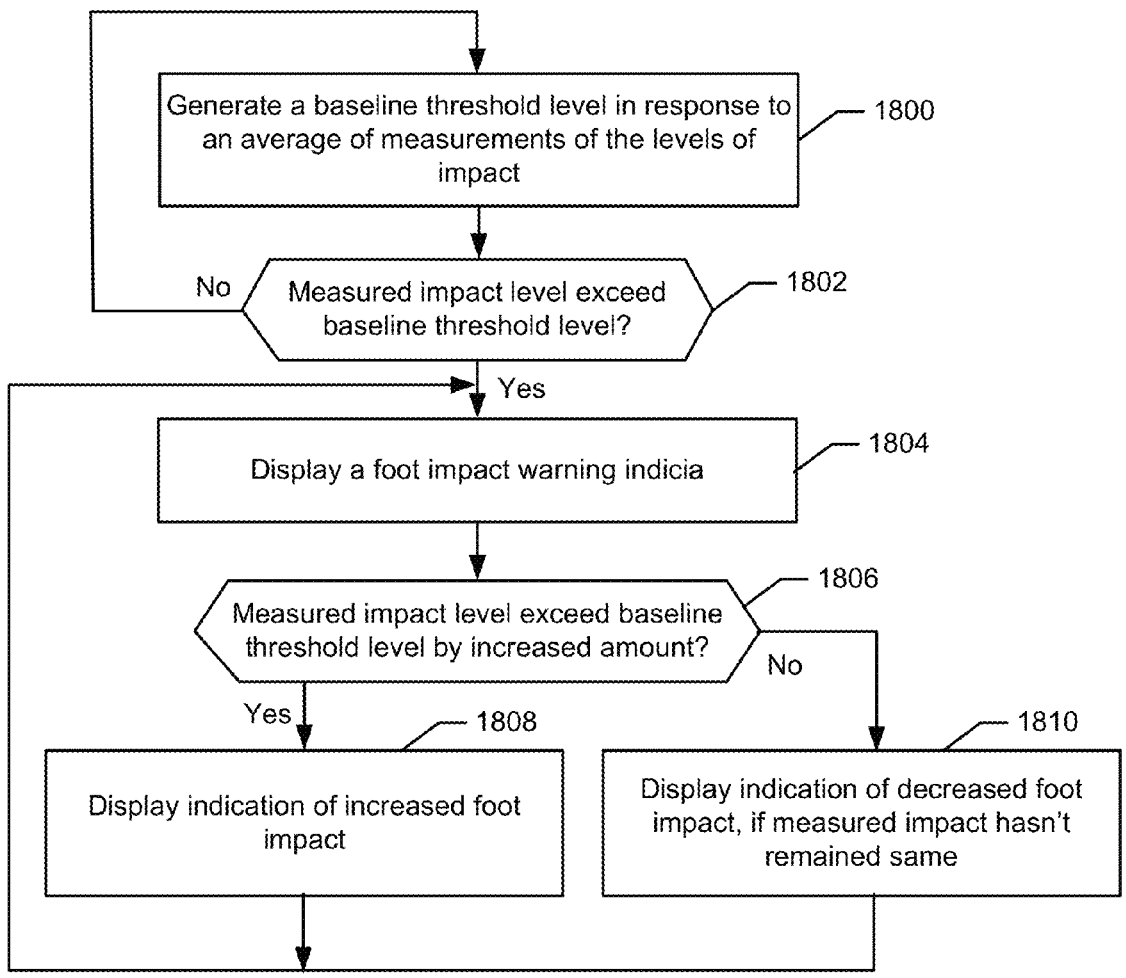
FIG. 18 is a flowchart of operations and methods that generate visual indicia that notify a runner/walker of measured foot impact levels while running/walking according to some embodiments of the present invention.

FIG. 18 is a flowchart of operations and methods for displaying a foot impact warning indicia (e.g., textual warning/symbol/etc.) to a person and regulates what is displayed responsive to measured levels of foot impact while walking/running. Referring to FIG. 18, a foot impact alert circuit (e.g., alert circuit 1700) generates (block 1800) a baseline threshold level in response to an average of measurements of the levels of impact. A decision (block 1802) is made as to whether the measured impact level exceeds the baseline threshold level and, if so, a foot impact warning indicia is displayed (block 1804) to the person. The operations may include a further decision (block 1806) is made as to whether the measured impact level exceeds the baseline threshold level by an increasing or decreasing amount.

When the measured level of the impact exceeds the baseline threshold level by an increased amount, the impact alert circuit 1700 responds (block 1808) by displaying an indication that the level of impact from the foot striking the surface has increased. In contrast, when the measured level of the impact exceeds the baseline threshold level by a decreased amount, the impact alert circuit 1700 responds (block 1810) by displaying an indication that the level of impact from the foot striking the surface has decreased. When the measure level of the impact has not changed relative to the baseline threshold level, the displayed indication may be maintained that same as the indication from the previous iteration.

In some embodiments, the impact alert circuit 1700 may generate one or more of the foot impact information display(s) 20 of FIG. 1 or another display that operates to visually inform a person whether their feet are impacting a surface harder or softer.

In some embodiments, the impact alert circuit is further configured to inform the person of a rate of change of a peak pulse of the measured impact (e.g., the peak pulse shown in the example graph 700 of FIG. 7). The impact alert circuit may generate a baseline threshold level in response to an average of rate of change of the peak pulse of the measured impact, and may respond to a presently measured rate of change of the peak pulse of the measured impact exceeding the baseline threshold level by generating an audible warning through a sound generation device and/or a visual warning through a display device. Generating the warnings in response to the rate of change of the peak pulse may be advantageous because the rate of change of acceleration (e.g., jerk) can indicate the magnitude of shocks that are being transmitted through the person's muscular, tendon, and skeletal structure of the feet, legs, and body, and may be a more accurate predictor of the likelihood of that a running/walking related injury will result if remedial actions are not taken by the person. Accordingly, one, some, or all of the embodiments of the invention disclosed herein can be configured to operate responsive to the rate of change of the peak pulse of the measured impact.

In some further embodiments, the circuits and operations of FIGS. 11-18 may be configured to alternatively or additionally sense whether and how much the person is running/walking with a foot overpronation or supination, and to notify the person using audio and/or visual indications as described in one or more of FIGS. 11-18. Accordingly, the circuits and operations may notify the person of the existence or amount of overpronation/supination by controlling the level of a notification sound that is combined with a music/audio component (e.g., FIGS. 14-16), by controlling the relative loudness of the notification sound, and/or by controlling an alert display (e.g., FIGS. 17 and 18) responsive to the measured overpronation/supination of the foot striking the surface.

In the above-description of various embodiments of the present invention, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

Monitoring and Coaching a Person's Sideways Spacing Foot Placement and Roll

With a normal pronation foot roll, the outside part of the heel makes initial contact with the ground. The foot "rolls" inward (e.g., about fifteen percent) and comes in complete contact with the ground. The rolling in of the foot optimally distributes the forces of impact, and is an important movement for proper impact absorption.

With an overpronation foot roll, the outside of the heel makes the initial ground contact and then the foot rolls inward more than an ideal amount (e.g., more than fifteen percent). Overpronation can cause the foot and ankle to have problems stabilizing the body, and provide poor impact absorption, and at the end of the gait cycle, the front of the foot pushes/lifts off the ground using mainly the big toe and second toe, which then must do all the work.

With a supination (underpronation) foot roll, the outside of the heel makes initial contact with the ground and then inward movement of the foot occurs at less than an ideal amount (e.g., less than fifteen percent), with resulting forces of impact being concentrated on a smaller area of the foot (the outside part) and not efficiently distributed. In the push-off phase, most of the work is done by the smaller toes on the outside of the foot.

Because some types and extent of pronation foot roll are the underlying routine cause of serious injuries to many people due to their muscular and skeletal physical geometry, footwear manufacturers have created a tremendous business out of designing, manufacturing, and selling shoes that provide varying levels of rigidity from side to side in the soles of shoes to attempt to constrain the amount of sideways roll of a person's foot. Some such shoes are called motion control shoes and/or stability shoes. While this approach can provide some beneficial effects, constraining the rolling of a person's foot through the design of a shoe sole may create other stresses and strains that can contribute to these and/or other types of injuries. Essentially the undesirable muscular-skeletal forces to generate proper motion are unfortunately counteracted at the most distal portion of the leg, i.e., the sole of the shoe, which results in large body-generated and shoe-counteracted-generated forces, torque, stress, and strain. Moreover, such approaches do not address the underlying root cause of undesired sideways roll of a person's foot and are devoid of any instruction to the person for how the sideways roll can otherwise be changed to provide improved walking/running characteristics for the person.

Body geometry that can cause normal pronation, overpronation, or supination foot roll can include the distance across the hips, relative angle and strength of connection of bones, tendons, and muscles extending from the hip to the feet and, in particular, from the ankle to the foot. Long distance runners can develop unbalanced muscle strength and tendon lengths in the upper legs, lower legs, ankles, and feet that cause the feet to angle too far inward or outward as the foot swings forward and makes contact with a running surface and then presses forward to liftoff to take another step.

The present inventors have discovered that adjusting the sideways spacing in a sideways direction between forward paths of the person's feet (also referred to as "sideways spacing" for short) can change the sideways roll of the person's foot toward a preferred sideways roll of the person's foot while the person walks/runs. However, because of the quantity and complexity of the muscular and skeletal nerve feedback experienced by a person occurring simultaneous with the visual and audio feedback of the walking/running experience, the person is not capable of adequately determining in real-time and for a sustained duration how much sideways roll a person's foot is experiencing and, moreover, determining how the sideways roll can be changed to obtain a more preferred sideways rules for that person by changing the sideways distance between forward paths of the person's foot as the person is walking/running.

As disclosed herein and further explained below, some further embodiments are directed to a foot monitoring system that coaches a person how to adjust sideways spacing between the feet in order to obtain a desired amount of sideways foot roll as the person walks and/or runs ("walks/runs").

As used herein, the symbol "/" refers to "and/or". Sideways rolls is a natural phenomena that occurs during forward rolling progression as a person's foot rolls forward from an impact location to lift-off from a running surface while the person is walking/running. In some embodiments, a foot monitoring system determines that a person is leaning the foot (ankle) inward or outward at various measured angles when striking the surface and resulting in undesirable rotational forces exerted on the foot, ankle, and/or knee. The alert circuit can generate an audible/visual warning to the person that notifies the person of the foot leaning contact and may further provide an indication of the extent of the leaning (e.g., indicate supination (underpronation), neutral pronation, or overpronation).

For example, a person who places one foot in front of the other when contacting a running surface while running is more likely to run with excessive overpronation foot roll, where the outside of the heel makes the initial ground contact and then the foot rolls inward. This results from body geometry where the upper legs are separated by the hip distance, and then angle inward therefrom extending to the contact locations of the feet being placed one in front of the other to strike the running surface while running. When the plane along the bottom of the foot is naturally about perpendicular in an inward/outward direction relative to a plane extending side-to-side through the leg, the plane along the bottom of the foot will also be naturally angled inward, so that the outside of the heel or midfoot makes the initial ground contact. As the foot roll forward, the body weight shifts over the foot and compresses the inside of the foot downward (stretching the muscles and tendons and bowing the skeletal structure of the legs and feet) to cause an abrupt and substantial rolling of the foot inward toward the other foot. The other foot similar rolls in the opposite direction toward the foot that has lifted off the ground.

At another extreme, a person who maintains a sideways spacing of more than the hip width between the forward paths of the feet (i.e., foot contact points on the running surface have a sideways spacing greater than the person's hip width) when contacting a running surface while running is more likely to run with excessive underpronation foot roll, where the inside of the heel makes the initial ground contact and then the foot rolls outward (away from the other foot). This results from body geometry where the upper legs are separated by the hip distance, and then angle outward toward the contact locations of the feet being placed one in front of the other. As the foot roll forward, the body weight shifts over the foot and compresses the outside of the foot downward to cause an abrupt and substantial rolling of the foot outward away from the other foot. The other foot similar rolls in the opposite direction away the foot that has lifted off the ground.

Figure 19A:
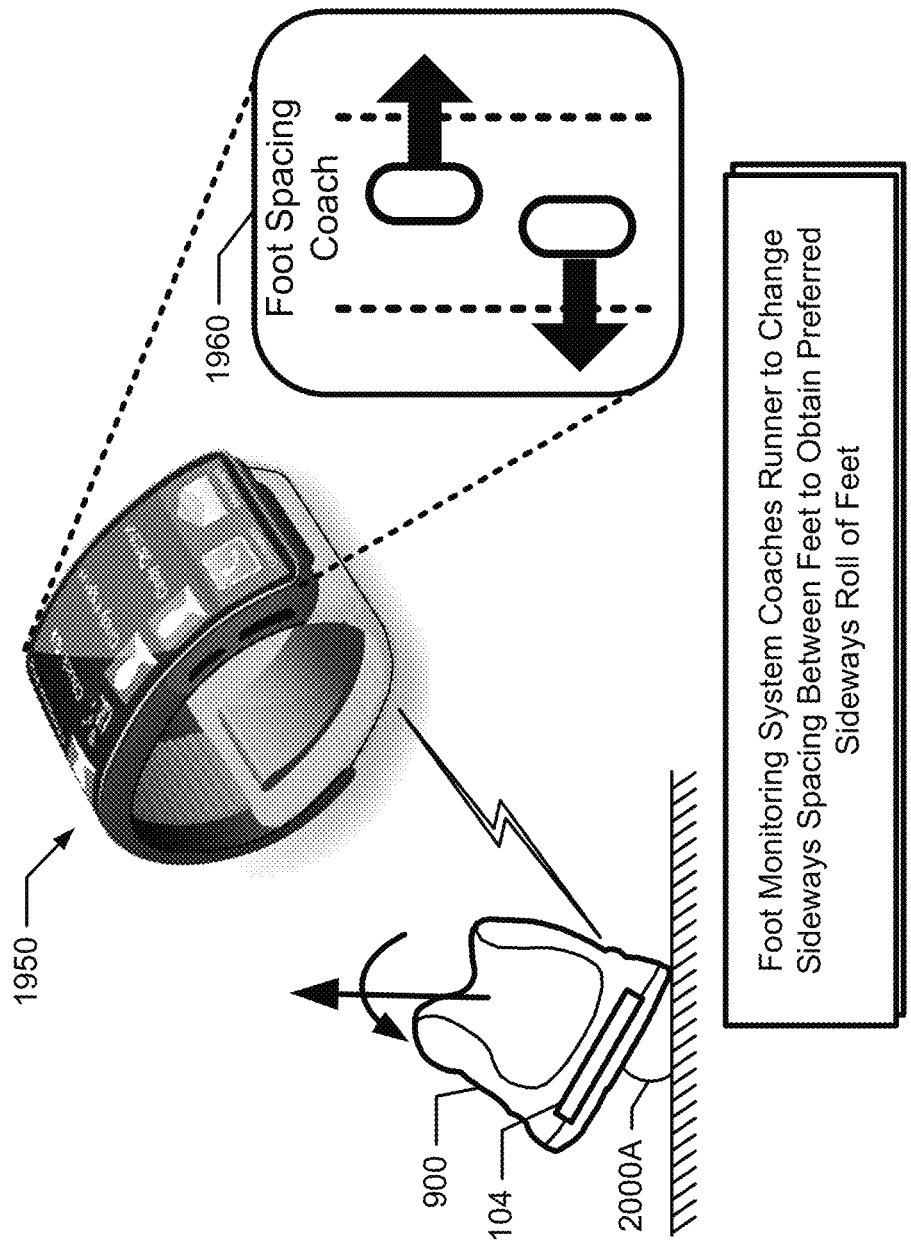
FIG. 19A illustrates a foot monitoring system that provides visual and/or audible coaching to runners/walkers to change sideways spacing between feet to obtain a more preferable sideways roll of the person's feet which the person runs/walks.

FIG. 19A illustrates a foot monitoring system that provides visual and/or audible coaching to runners/walkers to change sideways spacing between feet to obtain a more preferable sideways roll of the person's feet which the person runs/walks. Referring to FIG. 19A, the foot monitoring system includes a measurement circuit 104 connected to a shoe 900. The measurement circuit 104 may be within a removable insole within the shoe 900, within the sole of the shoe 900 (e.g., placed within a cutout portion of the sole or incorporated within the sole), and/or connected to the laces or another portion of the shoe 900.

The measurement circuit 104 measures sideways roll of a person's foot during at least a portion of forward rolling progression as the foot rolls forward from an impact location to lift-off from a running surface while the person is walking/running. The measurement circuit 104 communicates values of the measurements through a wireless interface to an alert circuit integrated within a wristwatch 1950 worn by the person. The alert circuit determines based on the sideways roll that the person should change sideways spacing in a sideways direction between forward paths of the person's feet to change further measured values of the sideways roll of the person's foot toward preferred sideways roll values of the person's foot while the person continues walking/running. The alert circuit generates an visual, tactile (e.g., vibration), and/or audible notification that indicates to the person to change the sideways spacing in the sideways direction between forward paths of the person's feet while the person continues walking/running. The further measured values of the sideways roll are measurements that have not yet occurred (i.e., the person hasn't yet taken those next steps), but are anticipated to occur if the person continues walking/running, so that the notifications provided by the alert circuit can coach the person as to how to favorably change those soon to be occurring footsteps as the person adjusts the sideways spacing between the feet.

In the example of FIG. 19A, the alert circuit displays in a foot spacing coach display area 1960 information that indicates to the person to change the sideways spacing in the sideways direction between forward paths of the person's feet while the person continues walking/running. Various operations and methods of the measurement circuit 104, the alert circuit, and the foot spacing coach information are described further below.

Although the measurement circuit 104 and alert circuit (e.g., wrist watch 1950) have been illustrated as being separate, their functionality may instead be at least partially integrated within a single device. Moreover, the alert circuit may be integrated within other devices than a wrist watch, such as a mobile phone, treadmill, table computer, etc.

In accordance with some embodiments, the foot monitoring system disclosed herein can provide audible, visual, vibration and/or other coaching (notifications) to a person as to what effect on sideways roll of the feet even small changes in the sideways spacing the person makes between the forward paths of the person's feet while walking/running. Thus, for example, a person can fine-tune the sideways spacing between their feet by one inch or several inches following notifications provided by the foot monitoring system to obtain a more preferable amount of sideways roll of the feet while running/walking.

In some further embodiments, the foot monitoring system can determine a preferable amount of sideways roll for the person and can provide guidance through notifications that allows the person to adjust the sideways spacing between the feet while walking/running to obtain the preferable amount of sideways roll. This real-time coaching can be provided through a wrist watch, mobile phone, treadmill, or other electronic device that the person can access while walking/running, and/or may be provided after the walking/running activity has been completed (e.g., such as through a personal computer, tablet computer, Internet analysis website accessible to the user).

The foot placement informational display 40 of FIG. 1 can provide information on whether the person is running/walking with overpronation or supination when the feet are impacting the surface, and may further indicate a relative amount of overpronation or supination that is occurring. For example, the information display 40 may include a graph 46,48 with a movable marker 49 that is moved along the graph 46,48 to indicate whether and to what extent the foot is impacting a surface with overpronation (distance of marker 49a along line 46 from ideal foot plant angle represented by vertical line), and to indicate whether and to what extent the foot is impacting a surface with supination (distance of marker 49*b* along line 48 from ideal foot plant angle represented by vertical line). The ideal foot plant angle may be calibrated for a particular person to compensate for the unique skeletal-muscular structure of a person that dictates what is a comfortable foot plant angle for that person. The calibration may be carried out in response to a user command while the person while running/walking with a comfortable foot placement sideways spacing, or may be carried out as an average or other numeric combination of sensed impact valued over a defined time period.

Figure 24:
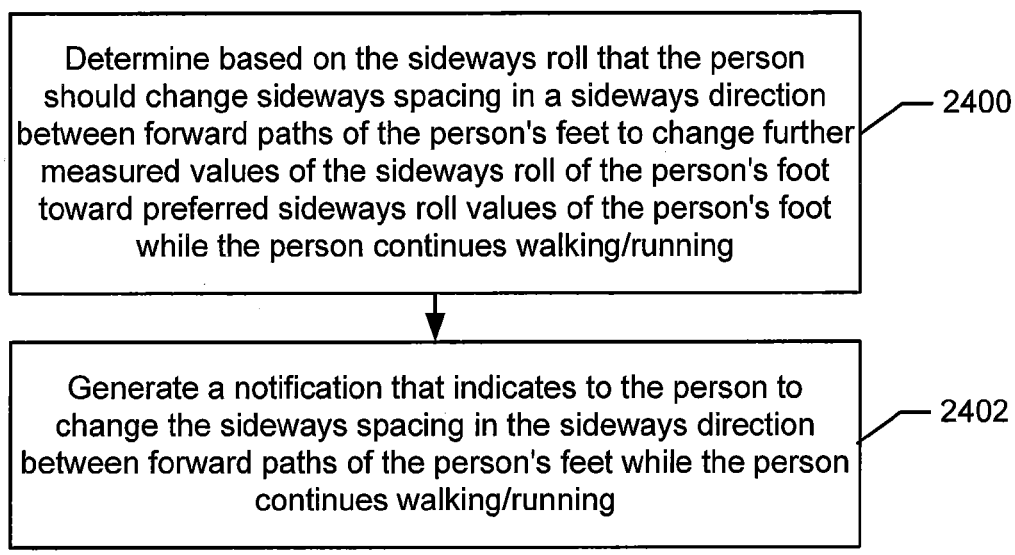
FIG. 24 is a flowchart of operations and methods that generate a notification that indicates to the person to change the sideways spacing in the sideways direction between forward paths of the person's feet while the person continues walking/running, according to some embodiments of the present invention.

FIG. 24 is a flowchart of operations and methods that can be performed by a foot monitoring system to generate a notification that indicates to the person to change the sideways spacing in the sideways direction between forward paths of the person's feet while the person continues walking/running, according to some embodiments. The foot monitoring system can include a measurement circuit and an alert circuit. The measurement circuit is configured to measure sideways roll of a person's foot during at least a portion of forward rolling progression as the foot rolls forward from an impact location to lift-off from a running surface while the person is walking/running. The alert circuit is configured to determine (block 2400) based on the sideways roll that the person should change sideways spacing in a sideways direction between forward paths of the person's feet to change further measured values of the sideways roll of the person's foot toward preferred sideways roll values of the person's foot while the person continues walking/running, and to generate (block 2402) a notification that indicates to the person to change the sideways spacing in the sideways direction between forward paths of the person's feet while the person continues walking/running.

The measurement circuit may be based on, incorporate features of, or be entirely different than the measurement circuit 104 described above with regard to FIG. 2, incorporated herein, and elsewhere. Thus, reference to element 104 which describing the measurement circuit does not limit the circuit to operations and methods described above for impact measurement. The measurements of sideways roll by the measurement circuit 104 may indicate an angular change (and may further indicate a direction of the angle, such as toward the inside or outside of the foot) of a plane through the shoe/foot between two spaced apart times during at least a portion of the forward rolling progression as the foot rolls forward from an impact location to liftoff from the running surface as the person is walking/running. Alternatively or additionally, the measurements of sideways roll by the measurement circuit 104 may indicate an angular rate of the sideways roll during at least a portion of forward rolling progression as the foot rolls forward from an impact location to lift-off from a running surface while the person is walking/running. Alternatively or additionally, the measurements of sideways roll by the measurement circuit 104 may indicate an angle between a plane through the shoe/foot and another reference plane (e.g., the running surface) during at least a portion of forward rolling progression as the foot rolls forward from an impact location to lift-off from a running surface while the person is walking/running (e.g., a tilt angle between shoe/foot and the running surface at initial contact or at a defined time thereafter).

The measurement circuit 104 may include an accelerometer that is configured to measure sideways roll of the person's foot during at least a portion of forward rolling progression as the foot rolls forward from an impact location to lift-off from a running surface while the person is walking/running. The measurement circuit 104 may further measure impact during at least a portion of forward rolling progression while the person is walking/running. Alternatively or additionally, the measurement circuit 104 may include a force transducer that is configured to measure sideways roll of the person's foot, and may further measure force during at least a portion of forward rolling progression as the foot rolls forward from an impact location to lift-off from a running surface while the person is walking/running. The force transducer may, for example, be configured to output a signal that indicates a measurement of the force, strain, and/or pressure in the material of the shoe 102 sole (e.g., rubber sole) as the material compresses/expands responsive to the foot rolling towards or away a side (e.g., from one side to another side, or from a neutral impact rolling toward him inward or outward side of the shoe).

The measurement circuit 104 may additionally or alternatively include a tilt sensor that measures angle/tilt, change of angle/tilt, and/or rotational rate, etc. (referred to as sideways roll) of the shoe/foot/leg when the foot rolls sideways during at least a portion of forward rolling progression as the foot rolls forward from an impact location to lift-off from a running surface while the person is walking/running, and may communicate values of the measured sideways roll to the alert circuit for use in generate a notification that indicates to the person to change the sideways spacing in the sideways direction between forward paths of the person's feet while the person continues walking/running. The tilt sensor may include, but is not limited to, a multi-axis accelerometer, a multi-axis force transducer, mechanical movement device (e.g., rolling ball with position sensors), or other inclinometer or sensor. The measurement circuit 104 may include one multi-axis sensor or may include spaced apart single-axis or multi-axis impact sensors (e.g., spaced apart in the direction of forward movement of the shoe 102 and/or spaced apart in a sideways direction to forward movement of the shoe 102) that can measure sideways roll (e.g., rolling from an outside impact region to an inside lift-off region of the shoe 102, rolling from an inside impact region to an outside lift-off region of the shoe 102, rolling from a more middle impact region to an inside or outside lift-off region of the shoe 102) of a person's foot during at least a portion of forward rolling progression as the foot rolls forward from an impact location to lift-off from a running surface while the person is walking/running.

The measurement circuit 104 may reside in one or more discrete packages that are, for example, connected to the shoe 102, and/or it may include a plurality of sensor elements that are spaced apart on the shoe 102 to, for example, measure characteristics of the sideways roll of a person's foot during at least a portion of forward rolling progression as the shoe rolls inward/outward (e.g., due to pronation/supination) after impacting the surface. Accordingly, sensor elements may be spaced apart at locations across a heel portion and/or across a midfoot/forefoot location of the shoe, and/or sensor elements may be spaced apart at locations in a right and left portion of the shoe.

In a further embodiment, at least a portion of the measurement circuit may be integrated within a permanent or removable shoe insole that can be placed within a shoe, residing underneath a person's foot when the shoe is worn. Integrating at least a portion of the measurement circuit into a shoe insole can increase the sensitivity and accuracy with which sideways roll of the person's foot can be measured, because rolling movement of the foot can be more directly sensed without possible obscuring of the movement by layers of upper and/or lower layers of foam/gel/material of the shoe that may otherwise exist between the persons foot and sensor elements of the measurement circuit. The sensor elements may be spaced sideways across the shoe insole to measure the amount and/or rate at which sideways roll of the foot is occurring. The sensor elements may be electrical switches that are closed by compressive force as the foot presses harder on them, and may be spaced across the shoe to provide a series of switch closings as the foot rolls across the corresponding switches.

The measurement circuit 104 may include a transmitter circuit 104a that transmits the measured impacts to the alert circuit 106, which includes a receiver circuit 106a to receive the measurements. The measurements may be transmitted through a wireless air interface using one or more wireless protocols, such as, without limitation, Bluetooth, near field communication (NFC), WIFI (e.g., IEEE 802.11), magnetic transmission, etc. The measurement circuit 104 may be configured to be mounted/connected/embedded within a heel (rear) region of the person's shoe to increase sensitivity of the measurements of sideways roll of the person's foot during at least a portion of the forward rolling progression. Although the measurement circuit 104 is illustrated in FIG. 2 as being within a heel region of the shoe, the invention is not limited thereto because the measurement circuit 104 may reside in a mid-foot region or forefoot region of the shoe 102 or may be connected elsewhere on a person's body. For example, the measurement circuit 104 may be configured to be connected a person's ankle or leg (e.g., via a strap) or elsewhere that will provide sufficient sensitivity to measure sideways rolling of a person's foot which may be determined from sideways movement of the person's leg and/or hip.

The alert circuit 106 is configured to determine based on the sideways roll that the person should change sideways spacing in a sideways direction between forward paths of the person's feet to change further measured values of the sideways roll of the person's foot toward preferred sideways roll values of the person's foot while the person continues walking/running, and to generate a notification that indicates to the person to change the sideways spacing in the sideways direction between forward paths of the person's feet while the person continues walking/running.

The alert circuit 106 may provide other information regarding foot placement on the surface, such as whether/how much the foot is impacting the surface tilted to the right of left at impact, what direction the foot is rolling after initial impact, how much the foot is rolling after initial impact, and/or how quickly the foot is rolling after initial impact.

Figure 19B:
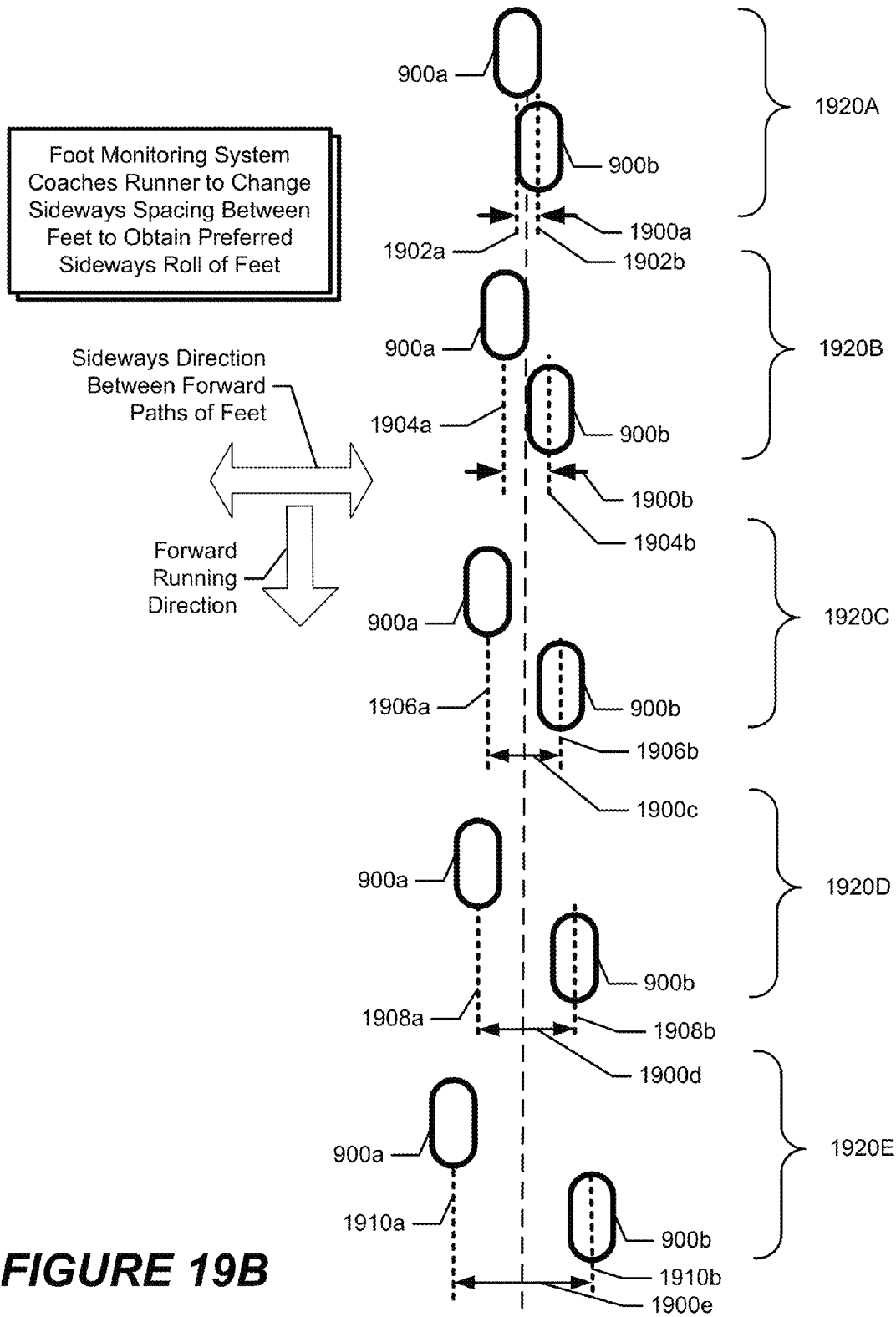
FIG. 19B illustrates a sequence of steps taken by a person while following guidance provided by notifications generated by a foot monitoring system operating according to some embodiments of the present invention.

FIG. 19B illustrates a sequence of steps 1920A-1920E taken by a person while following guidance provided by notifications generated by a foot monitoring system operating according to some embodiments of the present invention. Although a sequence of five pairs of step contact points 1920A-1920E with a running surface are illustrated for convenience of illustration and explanation, it is to be understood that other (and perhaps many other) steps may occur between any of the sequence of illustrated steps.

For this example, the forward running direction is illustrated downward from the top of the page toward the bottom. The right foot contact point 900a and left foot contact point 900b for a first one of the steps 1920A has a sideways spacing 1900a in a sideways direction between forward paths of the feet (right foot 900a forward path 1902a, and left foot 900b forward path 1902b). The sideways spacing 1900a is relatively small with one foot being placed nearly directly in front of the other foot as the person is running. As explained above, this may result in excessive overpronation foot roll, where the outside of the heel of one foot makes the initial ground contact and then, as the body weight shifts over the foot and compresses the inside of the foot downward (stretching the muscles and tendons and bowing the skeletal structure of the legs and feet), the foot experiences an abrupt and substantial sideways roll inward toward the other foot.

The foot monitoring system operates with the measurement circuit to measure the sideways roll of the person's foot during at least a portion of forward rolling progression as the foot rolls forward from an impact location to lift-off from a running surface while the person is walking/running. The alert circuit determines based on the sideways roll that the person should increase the sideways spacing in a sideways direction between forward paths of the person's feet to reduce the amount of inward sideways roll that the feet are experiencing while the person continues walking/running. The alert circuit responsively generates a notification that indicates to the person to increase the sideways spacing in the sideways direction between forward paths of the person's feet while the person continues walking/running.

Figure 20A:
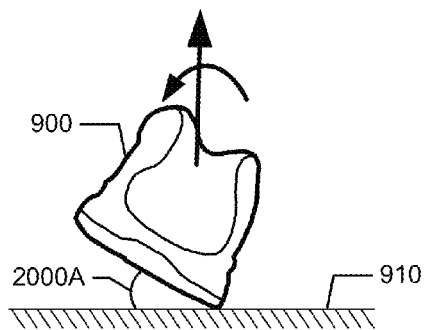
FIGS. 20A-E illustrate a sequence of impact angles and associated sideways roll of a person's foot during a portion of forward progression as the foot rolls forward from an impact location to lift-off from the running surface while the person is walking/running.

Referring to FIG. 20A, the initial contact angle 2000A of the right shoe 900a with the running surface 910 is excessive, causing the excessive overpronation foot roll as the foot rolls inward to a flat contact with the running surface 910 as the body weight shifts over the foot and compresses the inside of the foot downward (stretching the muscles and tendons and bowing the skeletal structure of the legs and feet).

Figure 21A:
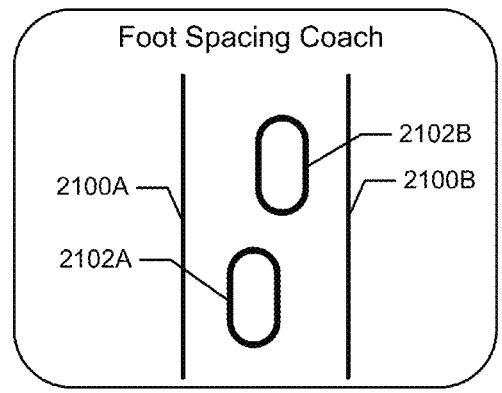
FIGS. 21A-E illustrate a sequence of notifications that are displayed on a display device of a foot monitoring system to provide visual notifications to the person responsive to values of measurements of the sideways roll of the person's foot corresponding to FIGS. 20A-E.

The foot monitoring system can respond to the determination that the person should increase sideways spacing by displaying on a display device the notification information shown in FIG. 21A to indicate to the person that the spacing should be increased and about how far the spacing should be increased. Referring to FIG. 21A, the displayed graphical indicia for the feet 2102A and 202B respectively represent the left and right feet, and the lines 2100A and 2102B represent the forward direction of movement of the feet and a preferred sideways spacing that the distance between the person's feet should be increased to. Thus, the gap between the left foot indicia 2102A and the left line 2100A indicate to the person that a relatively large increase in sideways spacing is needed, and which his similarly illustrated by the gap between the right foot indicia 2102B and the right line 2100B.

In this example, the person should increase the distance between the feet until the foot monitoring system displays the left foot indicia 2102A overlapping the left line 2100A and, similarly, the right foot indicia 2102B overlapping the right line 2100B.

Figure 20B:
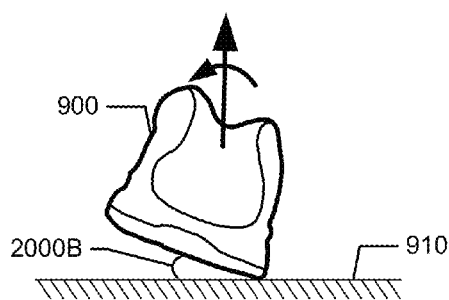
Figure 21B:
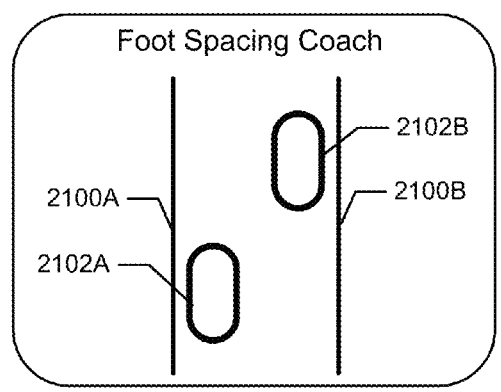

The person observes the notification and follows the coaching by slightly increasing the sideways spacing between feet to the distance 1900b between the forward paths 1904a-b shown in bracketed step 1920B. Referring to FIG. 20B, the initial contact angle 2000B of the right shoe 900a with the running surface 910 has decreased, causing the less-excessive overpronation foot roll as the foot rolls inward to a flat contact with the running surface 910. However, the alert circuit of the foot monitoring system determines from the values of the measured sideways roll that the sideways spacing of the feet should be further increased. The alert circuit therefore displays information in FIG. 21B with a smaller gap between the left foot indicia 2102A and the left line 2100A to indicate to the person that a smaller increase in sideways spacing is needed, and as similarly illustrated by the smaller gap between the right foot indicia 2102B and the right line 2100B.

Figure 20C:
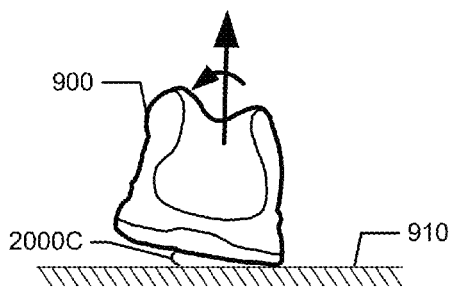
Figure 21C:
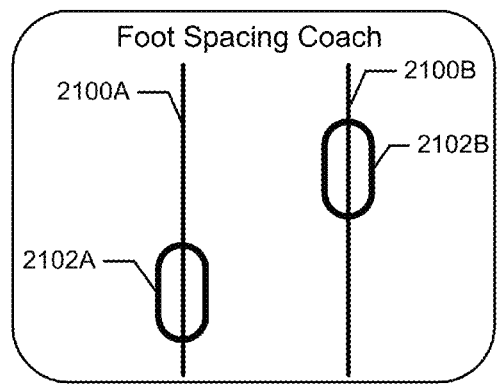

The person continues to observe the notification and follows the coaching by increasing the sideways spacing a little more between feet, which results in the sideways spacing distance 1900c between the forward paths 1906a-b shown in bracketed step 1920C. Referring to FIG. 20C, the initial contact angle 2000C of the right shoe 900a with the running surface 910 has decreased to a preferred amount of neutral pronation (e.g., less than about 15 degrees or another preferable amount that can be defined or determine for the person). The alert circuit of the foot monitoring system determines from the values of the measured sideways roll that the sideways spacing of the feet should be maintained by the person as the person continues running. The alert circuit therefore displays information in FIG. 21C with the left foot indicia 2102A relatively centered on the left line 2100A to indicate to the person that the sideways feet spacing is fine as-is and should be maintained, and as similarly illustrated by the right foot indicia 2102B relatively centered on the right line 2100B.

Figure 20D:
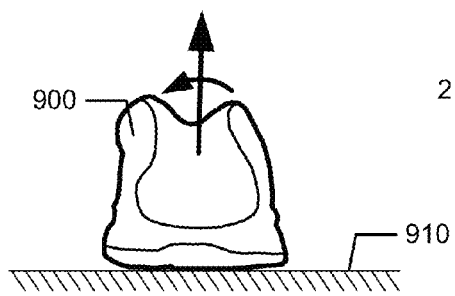
Figure 21D:
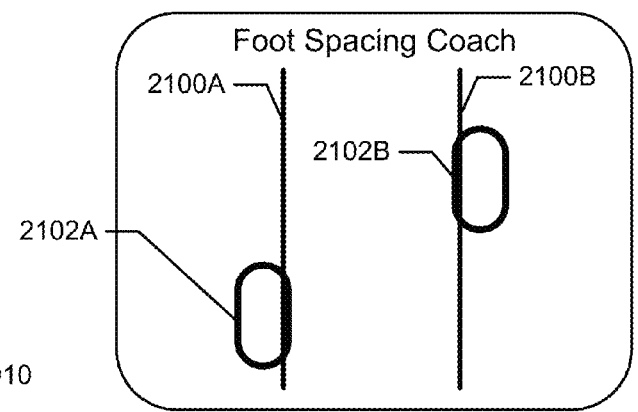

For the same person, perhaps as the person continues running and becomes more fatigued, or another person, the sideways spacing between the feet is excessive, as shown by the sideways spacing distance 1900d between the forward paths 1908a-b in FIG. 19. The resulting effect on the feet (e.g., as illustrated in FIG. 20D for the right foot 900a) is that the feet can strike the running surface 910 with no initial angle between the bottom of the foot and the surface, which, as explained above, may not be ideal for the person because of the reduced shock absorption provided. The alert circuit of the foot monitoring system determines from the values of the measured sideways roll that the sideways spacing of the feet should be decreased by the person as the person continues running. The alert circuit therefore displays information in FIG. 21D with the left foot indicia 2102A to the left of the left line 2100A to indicate to the person that the sideways feet spacing should be slightly decreased, and as similarly illustrated by the right foot indicia 2102B to the right of the right line 2100B.

Figure 20E:
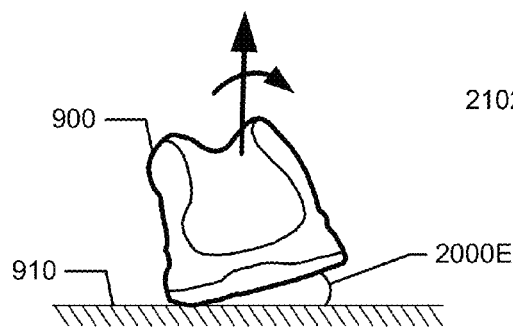

As the person continues running and becomes more fatigued, the sideways spacing between the feet has become more excessive in bracketed step 1920E relative to bracketed step 1920D, as shown by the sideways spacing distance 1900e between the forward paths 1910a-b in FIG. 19. The resulting effect on the feet (e.g., as illustrated in FIG. 20E for the right foot 900a) is that the inside edge of the feet can strike the running surface 910 with an initial angle 2000E between the bottom of the foot and the surface (oppositely directed than the angle 2000A of FIG. 20A), which causes the feet to roll outward away from each other as the body weight shifts over the foot and compresses the outside of the foot downward (stretching the muscles and tendons and bowing the skeletal structure of the legs and feet). The right foot 900a therefore can experience an abrupt and substantial sideways roll outward away from the left foot.

Figure 21E:
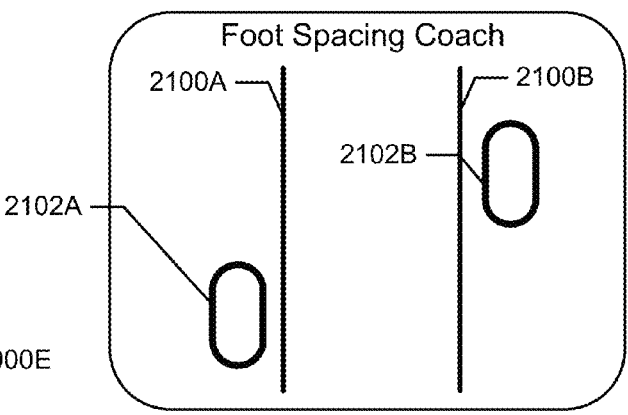

The alert circuit of the foot monitoring system determines from the values of the measured sideways roll that the sideways spacing of the feet should be decreased by the person as the person continues running. The alert circuit therefore displays information in FIG. 21E with the left foot indicia 2102A displayed further to the left of the left line 2100A to indicate to the person that the sideways feet spacing should be decreased (with the gap between the left foot indicia 2102A and the left line 2100A indicating a relative distance that the spacing should be decreased), and as similarly illustrated by the right foot indicia 2102B displayed further to the right of the right line 2100B.

Although various embodiments of the foot monitoring system and associated notifications which can be displayed on a display device to provide foot spacing coaching to a person are described in the context of FIGS. 19-21, other embodiments are not limited thereto. For example, FIGS. 22 and 23 illustrate other example embodiments of foot spacing coaching information that an alert circuit of a foot monitoring system can be displayed on a display device as notifications to coach a runner/walker to change sideways spacing the sideways direction between forward paths of the person's feet to provide more preferable sideways roll for the person's foot while the person continues walking/running.

Figure 22:
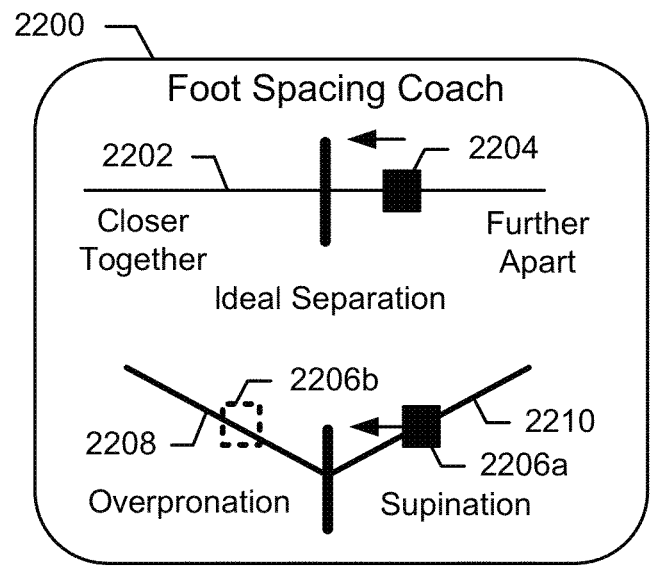
FIGS. 22 and 23 illustrate example foot spacing coach information that can be displayed on a display device by a foot impact monitoring system to coach a runner/walker to change sideways spacing in the sideways direction between forward paths of the person's feet to provide more preferable sideways roll for the person's foot while the person continues walking/running, according to some embodiments of the present invention.
Figure 23:
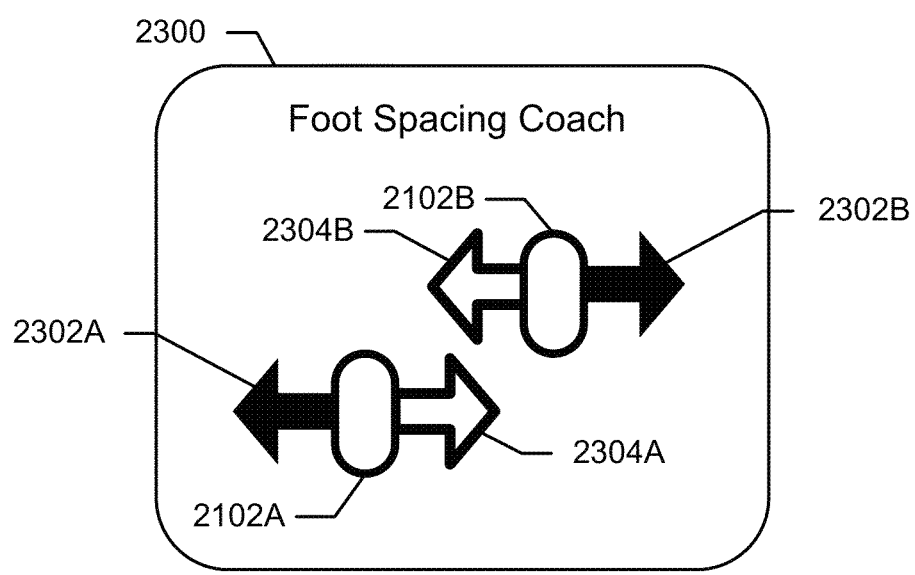

Referring to the upper graph in FIG. 22, the foot spacing coach information can include displaying a vertical line that represents an ideal separation between the forward paths of the person's feet. An indicia 2204 is graphed on a horizontal axis 2202 extending through the vertical line, with the distance between the indicia 2204 in the vertical line indicating a relative distance that the sideways spacing of the feet is recommended to be changed. Displaying the indicia 2204 to the right of the vertical line can indicate to the person that the feet are presently further apart than the ideal separation distance (and therefore should be moved closer together as a person continues walking/running) and, similarly, displaying the indicia 2204 to the left of the vertical line can indicate to the person that the feet are presently closer together than the ideal separation distance (and therefore should be moved further apart as a person continues walking/running).

Referring to the lower graph in FIG. 22, the foot spacing coach information can include displaying sloped lines which meet at a vertical line representing when an ideal separation between the forward paths of the person's feet occurs to provide a preferable amount of sideways roll of the feet. An indicia 2206a is displayed on the slope line 2210 to the right of the vertical line to indicate that the person's feet are presently rolling with an undesired level of supination, and therefore the sideways spacing between the feet should be changed to cause the indicia 2206a to move closer to the vertical line. In contrast, the indicia 2206b is displayed on the slope line 2208 to the left of the vertical line to indicate that the person's feet are presently rolling with an undesired level of overpronation, and therefore the sideways spacing between the feet should be changed to cause the indicia 2206b to move closer to the vertical line.

The person may thereby observe the upper and/or lower graphs (one or both of which may be displayed on a display device) to receive real-time coaching from the foot monitor system as to the preferable sideways spacing that the person should achieve between the person's feet while walking/running to obtain a preferable amount of sideways roll of the feet.

Referring to FIG. 23, the foot spacing coach information can include displaying one or more foot indicia with arrows extending away from the foot indicia or toward the indicia to indicate to the person whether the sideways distance between the feet should be increased or decreased to obtain a preferable amount of sideways roll of the feet. In the particular example of FIG. 23, a left foot indicia 2102A is displayed spaced apart from a right foot indicia 2102B. The alert circuit of the foot monitoring system can display a notification to the person to increase the spacing between the feet by displaying arrows 2302A and 2302B pointing away from each other. Similarly, the alert circuit of the foot monitoring system can display a notification to the person to decrease the spacing between the feet by displaying arrows 2304A and 2304B pointing toward each. The lengths of the arrows 2302A/B and 2304A/B can be controlled to indicate a relative sideways distance that the person should change the sideways spacing in the sideways direction between forward paths of the person's feet to provide more preferable sideways roll for the person's foot while the person continues walking/running (e.g., longer arrow lengths indicates a greater desired change in sideways spacing between the feet).

Determining Changes in Sideways Spacing

In one embodiment, the alert circuit can determine a relative distance that the sideways spacing should be changed by the person to obtain a more preferable sideways roll of the person's foot. Based on a result of a difference between the measured value of the sideways rule and a baseline threshold value and/or based on a ratio of a measured value of the sideways roll and the baseline threshold value. The alert circuit can generate the notification based on the relative distance to indicate how far the person is recommended to change the sideways spacing in the sideways direction between forward paths of the person's feet while the person continues walking/running. Thus, for example, the relative distance determined by the alert circuit can be used to generate the notifications shown in FIG. 21A-E, FIG. 22, and/or FIG. 23.

In another embodiment, the alert circuit can determine the sideways spacing based on a calibration process that determines what a particular person finds to be an acceptable range of sideways spacing between forward paths of the person's fee for walking/running. Example operations and methods that may be performed by the alert circuit of a foot monitoring system are explained in the context of a flowchart of FIG. 25. The calibration process is initiated (block 2500) responsive to receiving a user input via a user interface and/or responsive to another defined event, such as reset of the alert circuit. The alert circuit notifies (block 2502) the person to change sideways spacing of the feet between what the user considers to be the greatest and the minimum user acceptable distances while walking/running. The operations of blocks 2500 and 2502 are optional, in that the further operations of FIG. 25 may be performed outside of any formal calibration process and may be performed without initially instructing a person to vary sideways spacing between any defined range.

The alert circuit receives (block 2504) input from the person (e.g., via a user interface, such as by the person pushing a button, selecting a touch screen indicia, etc) indicating that a first spacing, corresponding to one of a greatest or a least sideways spacing between forward paths of the person's feet that the user finds acceptable for walking/running, is occurring. The alert circuit records (block 2506) in memory a measured value of the sideways rolls associated with the first spacing. The alert circuit receives (block 2508) input from the person indicating that a second spacing, corresponding to the other one of the greatest or the least sideways spacing between forward paths of the person's feet that the user finds acceptable for walking/running, is occurring. The alert circuit records (block 2510) in the memory a measured value of the sideways roll associated with the second spacing. The alert circuit determines (block 2512) a preferred value of sideways roll for the person based on the recorded measured values of sideways roll associated with the first and the second spacings. The alert circuit generates (block 2514) notifications to the person to change sideways spacing in the sideways direction between forward paths of the person's feet based on comparison of the preferred value of sideways roll and measured values of sideways roll while the person continues walking/running.

As explained above, with a normal pronation foot roll, the outside part of the heel makes initial contact with the ground. The foot "rolls" inward (e.g., about fifteen percent) and comes in complete contact with the ground. The rolling in of the foot optimally distributes the forces of impact, and is an important movement for proper impact absorption. In accordance with some further embodiments, the measurement circuit measures the level of impact that a foot is experiencing when striking the running surface, according to any one or more of the embodiments disclosed herein. The measured level of impact can occur anytime along the progression of the foot's impact with the running surface, i.e., from the initial contact through the body moving forward over the foot and causing increased forces thereon, and to lift-off (push-off) from the running surface. The alert circuit can determines from pairings of measured levels of impact and associated measured values of sideways rolls that are concurrently occurring while a person walks/runs, which one or more values of sideways roll are preferable for the person to walk/run with (e.g., values of sideways roll that occur when the corresponding sideways spacing between the feet is within a range known to be acceptable to the person while walking/running) to obtain a preferable level of impact for the person's feet (e.g., to reduce the level of impact or in some embodiments to minimize the level of impact). The alert circuit can determine that if higher values of sideways roll are occurring, which direction the sideways spacing between the feet needs to be changed to provide lower values of sideways roll, and vice versa, and can generate corresponding notifications to the person to change sideways spacing in the sideways direction to obtain a more preferable level of impact for the person's feet.

Accordingly, the alert circuit of the foot monitoring system can use the values of the impact and associated sideways roll measured by the measurement circuit (one or more circuits configured to measure the defined characteristics) to determine a preferable value of the sideways roll for the person (and which may be unique to the pair of shoes being worn by that person), and can generate the notifications to the person to change sideways spacing between the forward paths of the feet to obtain a more preferable level of impact for the person's feet.

Figure 25:
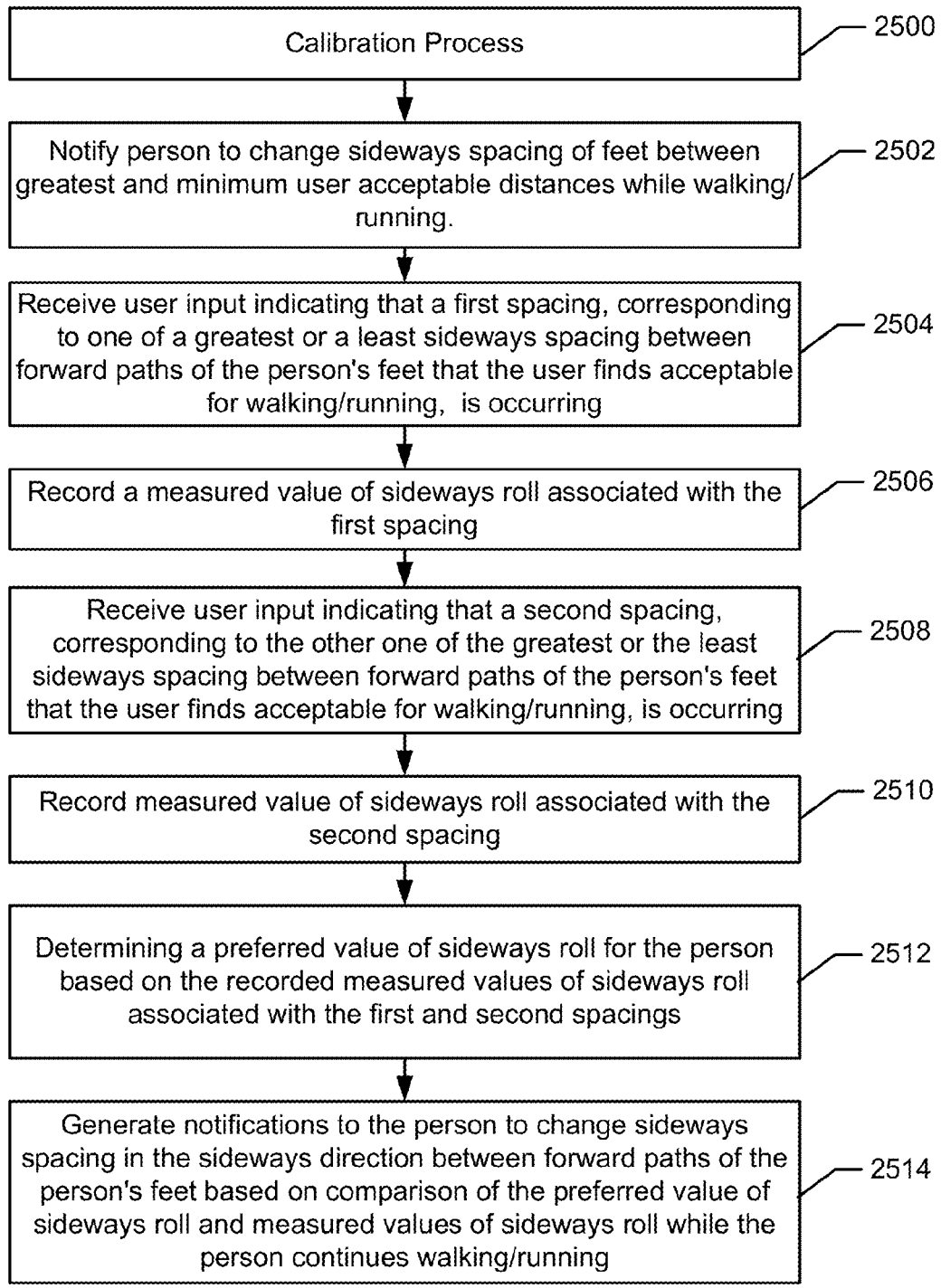
FIGS. 25-30 are a flowchart of operations and methods for determining a preferred value of sideways roll for a person's foot, and comparing the preferred value sideways roll to measured values of sideways roll while the person continues walking/running to generate notifications to the person to change sideways facing between forward paths of the person's feet, according to some embodiments of the present invention.

In a further embodiment with reference to FIG. 25, the alert circuit may also record the level of impact when recording (block 2506) the measured value of sideways roll associated with the first spacing, and may record the level of impact when recording (block 2510) the measured value of sideways roll associated with the second spacing. The alert circuit may then determine (block 2512) the preferred value of sideways roll based on the recorded levels of impact associated with the first and second spacings. For example, the alert circuit may determine a sideways roll that provides a preferable level of impact for the person wearing the particular pair of shoes, and can define the preferred value of sideways roll based on the determined sideways roll. The alert circuit can know that if higher values of sideways roll are occurring, which direction the sideways spacing between the feet needs to be changed to provide lower values of sideways roll, and vice versa.

Figure 26:
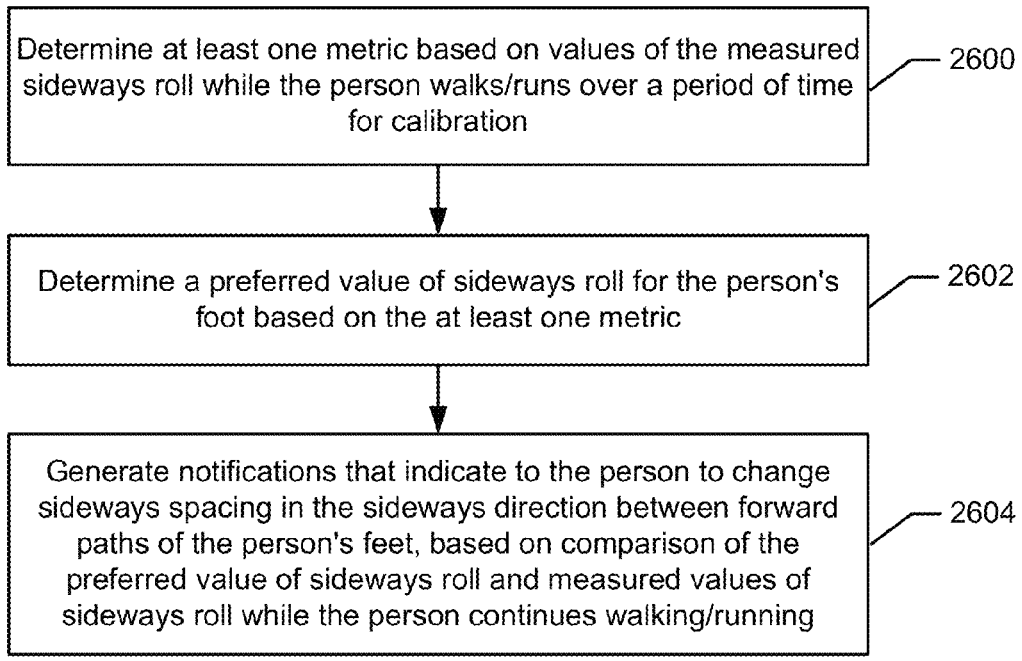

In another embodiment shown in FIG. 26, the alert circuit is configured to determine (block 2600) at least one metric based on values of the measured sideways roll while the person walks/runs over a period of time for calibration. The alert circuit determines (block 2602) a preferred value of sideways roll for the person's foot based on the at least one metric, and generates (block 2604) notifications that indicate to the person to change sideways spacing in the sideways direction between forward paths of the person's feet, based on comparison of the preferred value of sideways roll and measured values of sideways roll while the person continues walking/running.

Figure 27:
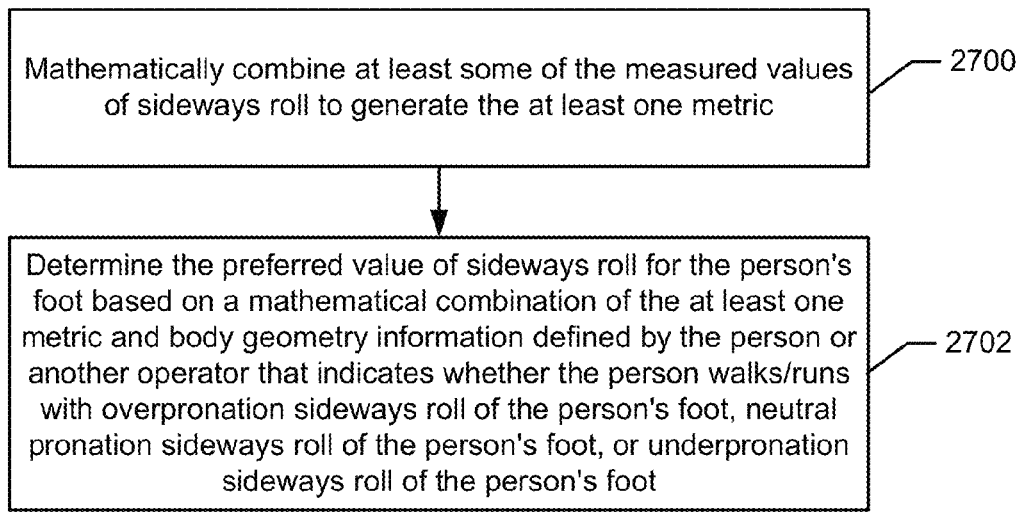

In a further embodiment shown in FIG. 27, the alert circuit mathematically combines (block 2700) at least some of the measured values of sideways roll (e.g., by averaging or other mathematical combination of a plurality of the measured values) to generate the at least one metric. The alert circuit determines (block 2702) the preferred value of sideways roll for the person's foot based on a mathematical combination of the at least one metric and body geometry information defined by the person or another operator that indicates whether the person walks/runs with overpronation sideways roll of the person's foot, neutral pronation sideways roll of the person's foot, or underpronation sideways roll of the person's foot.

Figure 28:
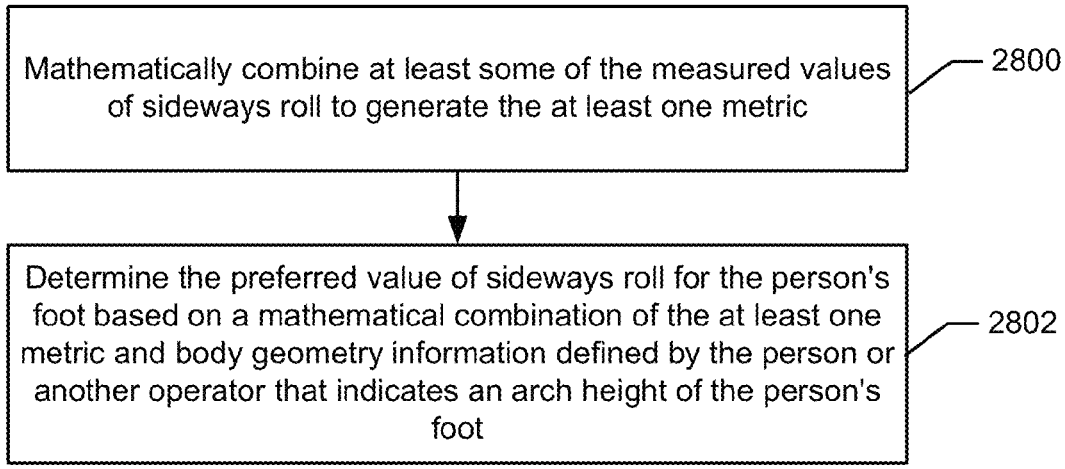

In a further embodiment shown in FIG. 28, the alert circuit mathematically combines (block 2800) at least some of the measured values of sideways roll to generate the at least one metric. The alert circuit determines (block 2802) the preferred value of sideways roll for the person's foot based on a mathematical combination of the at least one metric and body geometry information defined by the person or another operator that indicates an arch height of the person's foot.

Figure 29:
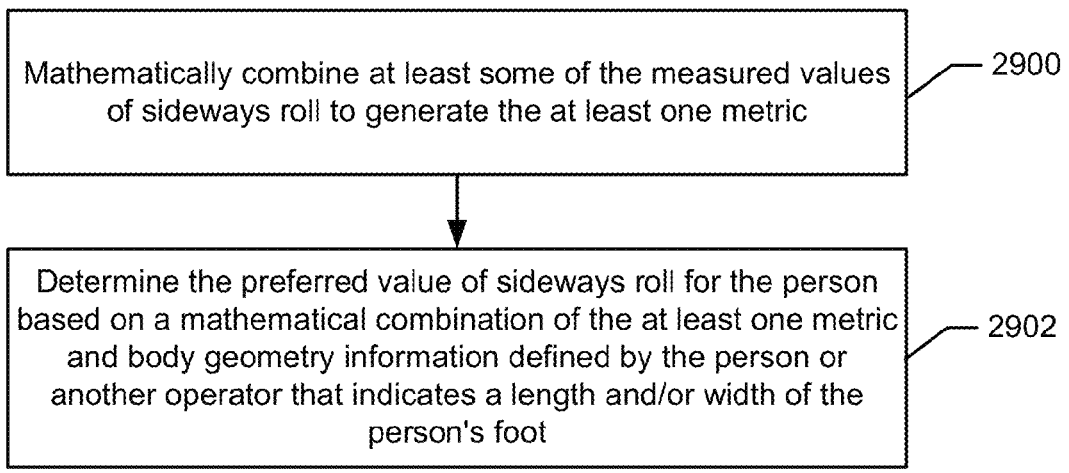

In a further embodiment shown in FIG. 29, the alert circuit mathematically combines (block 2900) at least some of the measured values of sideways roll to generate the at least one metric. The alert circuit determines (block 2902) the preferred value of sideways roll for the person based on a mathematical combination of the at least one metric and body geometry information defined by the person or another operator that indicates a length and/or width of the person's foot.

In a further embodiment, the alert circuit determines a range of the values of the measured sideways roll as the person walks/runs over the period of time, and generates the preferred value of sideways roll based on the range of the values.

One of more of the embodiments of FIGS. 26-29 can be combined with the measurement circuit (same or different from the measurement circuit that measures sideways roll) measuring values of impact according to one or more embodiments disclosed herein. The alert circuit determines from the values of impact associated with the concurrently measured values of the sideways roll, a preferred value of sideways roll for the person based on it providing a preferable level of impact. The preferred value of sideways roll may also be determined based on one or more conditions for the sideways spacing that occurs between the feet, which corresponding to when the value of sideways roll is obtained, being an acceptable amount of sideways spacing that the person has been observed walking/running with (e.g., during a threshold time of measurement) and/or which the person has provided input to the alert circuit indicating acceptability of the sideways spacing (e.g., the user indicating an acceptable range of sideways spacing via corresponding measured values of sideways roll while the person walks/runs with, for example, changing between a greatest and least spacing between the feet that the person feels is acceptable). The alert circuit generates the notifications to provide guidance to the person as to preferable changes in the sideways spacing of the person's feet that the person should perform to obtain preferable levels of impact as the person continues walking/running. The preferable level of impact may be a minimum impact that is obtainable at value of sideways roll of the feet that the person finds acceptable for walking/running.

Accordingly, the preferred value of sideways roll may be determined at least in part based on information provided by a person or another operator that indicates an amount of sideways roll that is acceptable for that person to sustain while running/walking with reduced risk of discomfort and injury. The preferred value of sideways roll may alternatively or additionally be determined based on analysis of humans in general or various classes of human, such as humans having a defined arch height, foot length, foot width, weight, foot motion from lift-off to forward strike (e.g., does the foot lift upward and swing forward without more than a threshold sideways arc), etc. The alert circuit can adjust one or more predefined values based on characteristics of the person to generate a preferred value of sideways roll.

Controlling Sideways Spacing of Feet to Regulate Sideways Roll and Foot Impact

In some further embodiments, the foot monitoring system measures the level of impact that a foot is experiencing when striking the running surface, and provides notifications to the person to change sideways spacing between the feet based on a combination of the measured impact and measured sideways roll of the foot.

The measurement circuit can be configured to measure impact during at least a portion of forward rolling progression as the foot strikes the running surface and rolls forward from an impact location to lift-off from the running surface while the person is walking/running, and may be configured to operate according to the operation and methods of any one or more of the embodiments disclosed herein for measuring impact, etc. The measurement circuit may be the same measurement circuit used to measure sideways roll of the foot or may be a separate discrete measurement circuit. Accordingly, as used herein "measurement circuit" may be one or more circuits that are configured to measured sideways roll, foot impact, and/or other conditions as disclosed herein.

Figure 30:
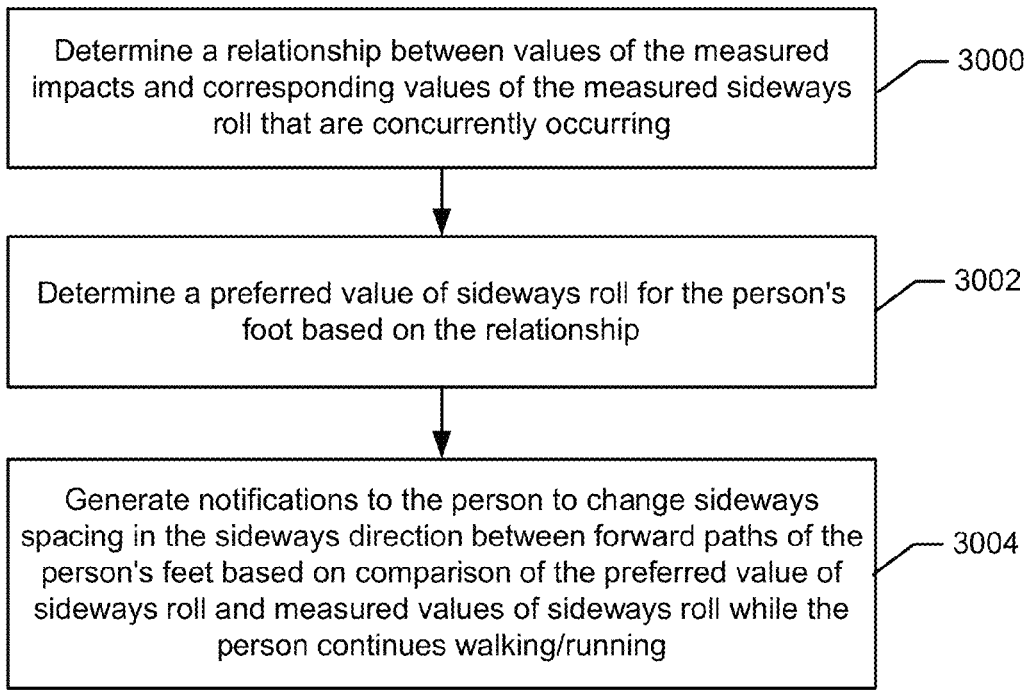

FIG. 30 is a flowchart of operations and methods that may be performed by the alert circuit in accordance with some embodiments. The alert circuit determines (block 3000) a relationship between values of the measured impacts and corresponding values of the measured sideways roll that are concurrently occurring. The alert circuit determines (block 3002) a preferred value of sideways roll for the person's foot based on the relationship, and generates (block 3004) notifications to the person to change sideways spacing in the sideways direction between forward paths of the person's feet based on comparison of the preferred value of sideways roll and measured values of sideways roll while the person continues walking/running.

In some further embodiments, the relationship determined by the alert circuit indicates a trend between changes in the values of the measured impacts and corresponding measured values of the sideways roll that are concurrently occurring. The alert circuit may, for example, identify a value of the sideways roll that corresponds to a preferable level of impact (e.g., based on interpolation or extrapolation among the measured values), and may define the preferred value of sideways roll based on the identified value of the sideways roll. The preferable level of impact may be a minimum impact that is obtainable at value of sideways roll of the feet that the person finds acceptable for walking/running.

The alert circuit may be configured to determine from the relationship the preferred value of sideways roll for the person to reduce values of the impacts while corresponding values of the sideways roll that are concurrently occurring satisfy a defined criteria as the person continues walking/running. Thus, alert circuit can coach a person on adjusting the sideways spacing between the feet to obtain a more acceptable level of foot impact (e.g., impact force/vibration/acceleration) while simultaneously obtaining an acceptable level of sideways roll.

The alert circuit may be configured to determine from the relationship the preferred value of sideways roll for the person to obtain preferable values of the sideways roll while corresponding values of the impact that are concurrently occurring satisfy a defined criteria as the person continues walking/running. Thus, alert circuit can coach a person on adjusting the sideways spacing between the feet to obtain a more preferable sideways roll while simultaneously obtaining an acceptable level of foot impact (e.g., impact force/vibration/acceleration).

The alert circuit may be further configured to generate a record of values of the measured sideways roll of the person's foot while the person is walking/running. The foot monitor system can include a display device that graphs the values of the measured sideways roll from the record relative to an elapsed time of the activity, a speed at which the person was walking/running, a stride step distance, and/or a distance that the person walked/ran.

Thus, the alert circuit can generate a balance between levels of foot impact and levels of foot sideways roll that satisfy one or more defined rules, which are based on the determined relationship between values of the measured impacts and corresponding values of the measured sideways roll that are concurrently occurring.

The alert circuit may be further configured to generate the notification by regulating a tone characteristic of an audible warning generated through a sound generation device to indicate to the person to change the sideways spacing in the sideways direction between forward paths of the person's feet while the person continues walking/running. For example, the alert circuit may increase a tone frequency to indicate that the sideways spacing between feet should be increased and decrease a tone frequency to indicate that the sideways spacing between feet should be decreased, or vice versa. By way of another example, the alert circuit may output a first sound to indicate that the sideways spacing between feet should be increased and output a different second sound to indicate that the sideways spacing between feet should be decreased. By way of another example, the alert circuit may increase an output sound to indicate that the sideways spacing between feet should be increased and decrease the output sound to indicate that the sideways spacing between feet should be decreased, or vice versa.

The alert circuit may be further configured to generate the notification by displaying a visual warning through a display device to indicate to the person to change the sideways spacing in the sideways direction between forward paths of the person's feet while the person continues walking/running.

The alert circuit may also regulate background sound that is combined with music being played to a person, such as described above, to generate the notifications of desired changes in sideways foot spacing.

As explained above, the measurement circuit may be configured to be mounted on the person's shoe to increase sensitivity of the measurement from the foot striking the surface while the person is walking/running, and the alert circuit can be incorporated into a wrist watch (e.g., electronic smart watch), a communication terminal (e.g., smart phone), a palmtop computer, a tablet computer, a laptop computer.

Predicting Remaining Shoe Cushioning Life

As explained in detail above, some embodiments are directed to a foot monitoring system that determines and displays how much useful cushioning life remains in shoes and/or when shoes no longer provide sufficient cushioning for continued running/walking. As shown in FIG. 1, the system can display indicia that indicate when a particular pair of running shoes no longer provides sufficient cushioning and should be replaced before onset of occurrence of one or more running related injuries. For example, a shoe outline (or other graphical object) 50 can be filled-in (or emptied) to graphically indicate how much cushioning life remains in a particular pair of shoes. A filled-in shoe outline 50 (or emptied outline) may thereby indicate that the shoes should be replaced because they no longer provide a sufficient level of cushioning.

Figure 31:
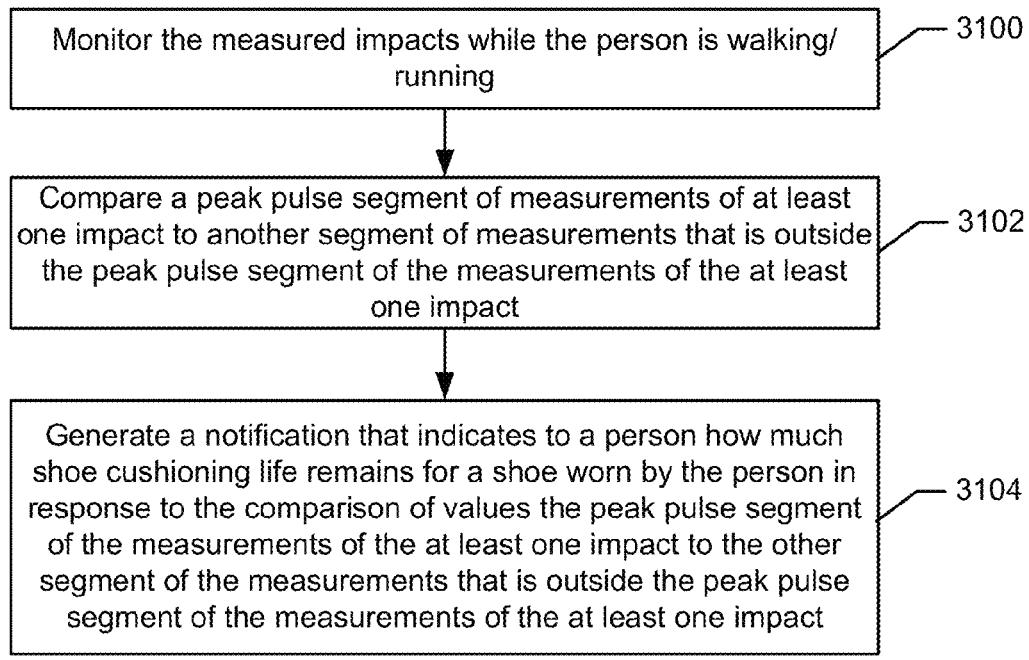
FIG. 31 is a flowchart of operations and methods for generating a notification that indicates to a person how much shoe cushioning life remains for a shoe worn by the person in response to comparison of values a peak pulse segment of measurements of at least one impact to another segment of the measurements that is outside the peak pulse segment of the measurements of the at least one impact, according to some embodiments of the present invention.

FIG. 31 is a flowchart of operations and methods that can be performed by a foot monitoring system for generating a notification that indicates to a person how much shoe cushioning life remains for a shoe worn by the person in response to comparison of values a peak pulse segment of measurements of at least one impact to another segment of the measurements that is outside the peak pulse segment of the measurements of the at least one impact, according to some embodiments.

The foot monitoring system can include a measurement circuit and an alert circuit. The measurement circuit is configured to measure impacts from a foot repetitively striking a surface while a person is walking/running. The alert circuit is configured to monitor (block 3100) the measured impacts while the person is walking/running. The alert circuit compares (block 3102) a peak pulse segment of measurements of at least one impact to another segment of measurements that is outside the peak pulse segment of the measurements of the at least one impact. The alert circuit generates (block 3104) a notification that indicates to a person how much shoe cushioning life remains for a shoe worn by the person in response to the comparison of values the peak pulse segment of the measurements of the at least one impact to the other segment of the measurements that is outside the peak pulse segment of the measurements of the at least one impact.

Thus, for example, referring to the graph 700 of FIG. 7. The graph 700 illustrates an example curve/trend in impact measurements during a single impact experienced by a foot relative to time from the foot striking a surface while a person is running. The impact force and acceleration rapidly increases from when the shoe initially impacts a surface (e.g., with a heel strike) to a peak magnitude, between time T1 and T2, as the sole of the shoe rapidly compresses to absorb some of the impact. The foot impact then more gradually decreases from the peak magnitude as the foot rolls forward (e.g., from a heel strike to mid-foot and then forefoot) compressing other regions of the sole of the shoe, and then the foot leaves the ground to be positioned for the next impact while the person is running/walking. In some embodiments, the alert circuit is configured to generate a notification that indicates to a person how much shoe cushioning life remains for a shoe worn by the person in response to comparison of values of a peak pulse segment of the measurements (e.g., between time T1 and T2) of the at least one impact to another segment of the measurements that is outside the peak pulse segment of the measurements of the at least one impact. For segment of the measurements that is outside the peak pulse segment may be, for example, from time of initial impact of the shoe with the running surface to time T1, from time T2 to time of lift-off of the shoe from the running surface, and/or from time of initial impact of the shoe with the running surface to time of lift-off of the shoe from the running surface, or another segment that is selected by the foot monitoring system.

The alert circuit may compare a magnitude, average, or other measurement associated with the peak pulse segment (e.g., between T1 and T2) to a magnitude, average, or other measurement of another segment of the impact (e.g., outside of the peak pulse (e.g., from T2 to the end of the measured impact) or inclusive of the peak pulse) to determine how much shoe cushioning life remains for the shoe as the person walks/runs. Because the measured impact level will vary with weight of the runner, comparison of a peak pulse segment to the entire impact waveform or another segment outside of the peak pulse segment may enable the alert circuit to at least partially remove bias that is introduced into the measurements due to the person's weight. The alert circuit may, for example, be configured to respond to an increase in the difference from the comparison by indicating to the person that the remaining shoe cushioning life has decreased a defined amount. The impact alert circuit may alternatively or additionally be configured to respond to a difference from the comparison exceeding one or more defined thresholds by determining that the remaining shoe cushioning life has correspondingly decreased, and displayed associated indicative indicia (graphical or textual indication on a display device) indicating to the person what the present shoe cushioning life is for the shoe.

As explained above, the alert circuit may determine the remaining shoe life based on comparison of the peak pulse segment and another segment that overlaps at least a portion of the peak pulse segment and extends beyond the peak pulse segment of the measurements of the at least one impact while the person is walking/running. The other segment can be an entire impact waveform of the measurements of the at least one impact while the person is walking/running, and the peak pulse segment of the measurements of the at least one impact is a subset of the measurements that includes a peak value of the measurements.

The alert circuit may generate the notification based on a ratio of at least one value of the peak pulse segment of the measurements to at least one value of the other segment of the measurements that is outside the peak pulse segment of the measurements.

The alert circuit may generate the notification based on a difference between at least one value of the peak pulse segment of the measurements and at least one value of the other segment of the measurements that is outside the peak pulse segment of the measurements.

The impact alert circuit may be configured to control an amount that an object displayed on a display device is filled-in or emptied to graphically indicate how much cushioning life remains in the shoe, such as by filling-in the shoe indicia 50 shown in FIG. 1.

As explained above, the measurement circuit may be configured to be mounted on the person's shoe to increase sensitivity of the measurement from the foot striking the surface while the person is walking/running, and the alert circuit can be incorporated into a wrist watch (e.g., electronic smart watch), a communication terminal (e.g., smart phone), a palmtop computer, a tablet computer, a laptop computer.

Figure 32:
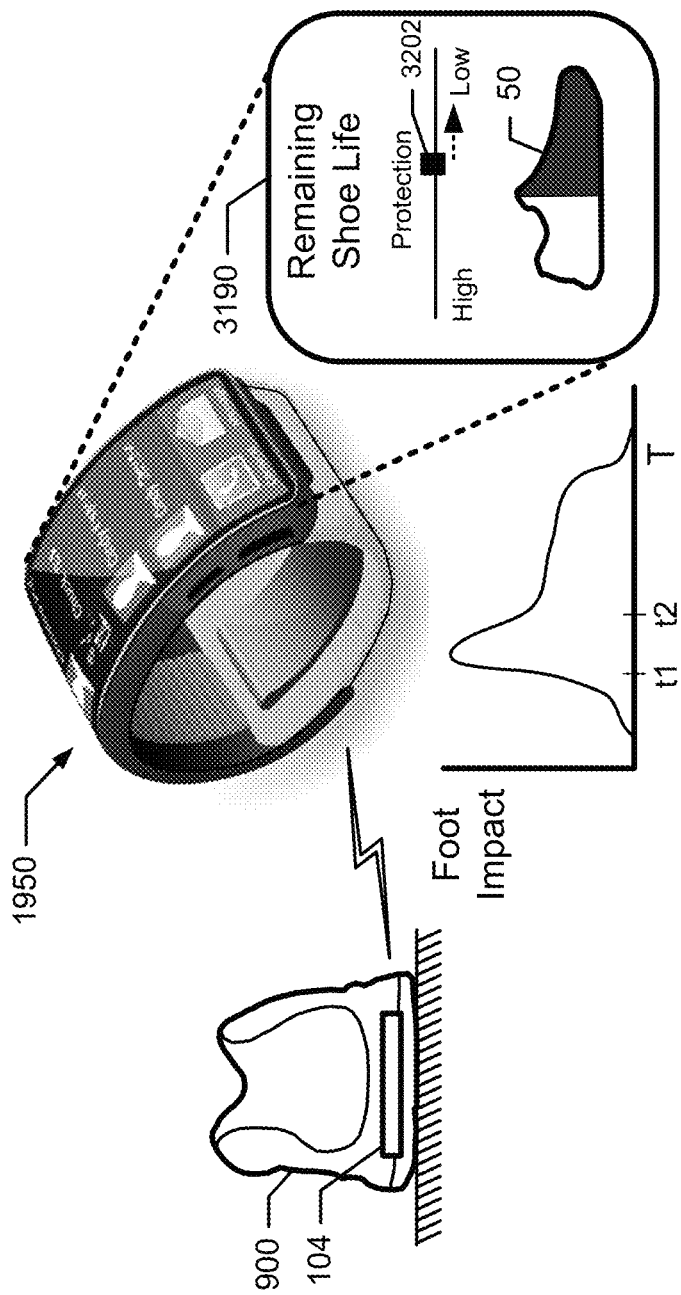
FIG. 32 illustrates a foot monitoring system that provides visual and/or audible indication to runners/walkers of the shoe cushioning life remaining in a shoe worn by the person, according to some embodiments of the present invention.

FIG. 32 illustrates an example foot monitoring system that visually displays remaining shoe life information in a display area 3190 and/or audibly indicates information to runners/walkers that indicates the shoe cushioning life remaining in a shoe worn by the person, according to some embodiments of the present invention. The foot monitoring system includes the measurement circuit 104 connected to a shoe 900. The measurement circuit 104 may be within a removable insole within the shoe 900, within the sole of the shoe 900 (e.g., placed within a cutout portion of the sole or incorporated within the sole), and/or connected to the laces or another portion of the shoe 900.

The measurement circuit 104 measures impact from a foot repetitively striking a surface while a person is walking/running, and communicates values of the measurements through a wireless interface to the alert circuit integrated within a wristwatch 1950 worn by the person. The alert circuit compares a peak pulse segment (e.g., between times t1 and t2) of measurements of at least one impact to another segment (e.g., before time t1, after time t2, or an time segment that extends at least partially beyond the range of time t1 to t2) of measurements that is outside the peak pulse segment of the measurements of the at least one impact. The alert circuit generate a visual and/or audible notification that indicates to a person how much shoe cushioning life remains for a shoe worn by the person in response to the comparison of values the peak pulse segment of the measurements of the at least one impact to the other segment of the measurements that is outside the peak pulse segment of the measurements of the at least one impact.

In the example of FIG. 32, the alert circuit displays the remaining shoe life by controlling an amount that an object 50 displayed on a display device that is filled-in or emptied to graphically indicate how much cushioning life remains in the shoe. Alternatively or additionally, the alert circuit may display the remaining shoe life by moving an object 3202 along a line that extends from one end ("High" protection indicia) to another end ("Low" protection indicia) to visually indicate when substantial cushioning life remains (e.g., object 3202 is placed near the "High" protection indicia), when little remaining cushioning life remains (e.g., object 3202 is placed near the "Low" protection indicia), and determinations therebetween.

Further Embodiments of a Foot Monitoring System

Figure 33:
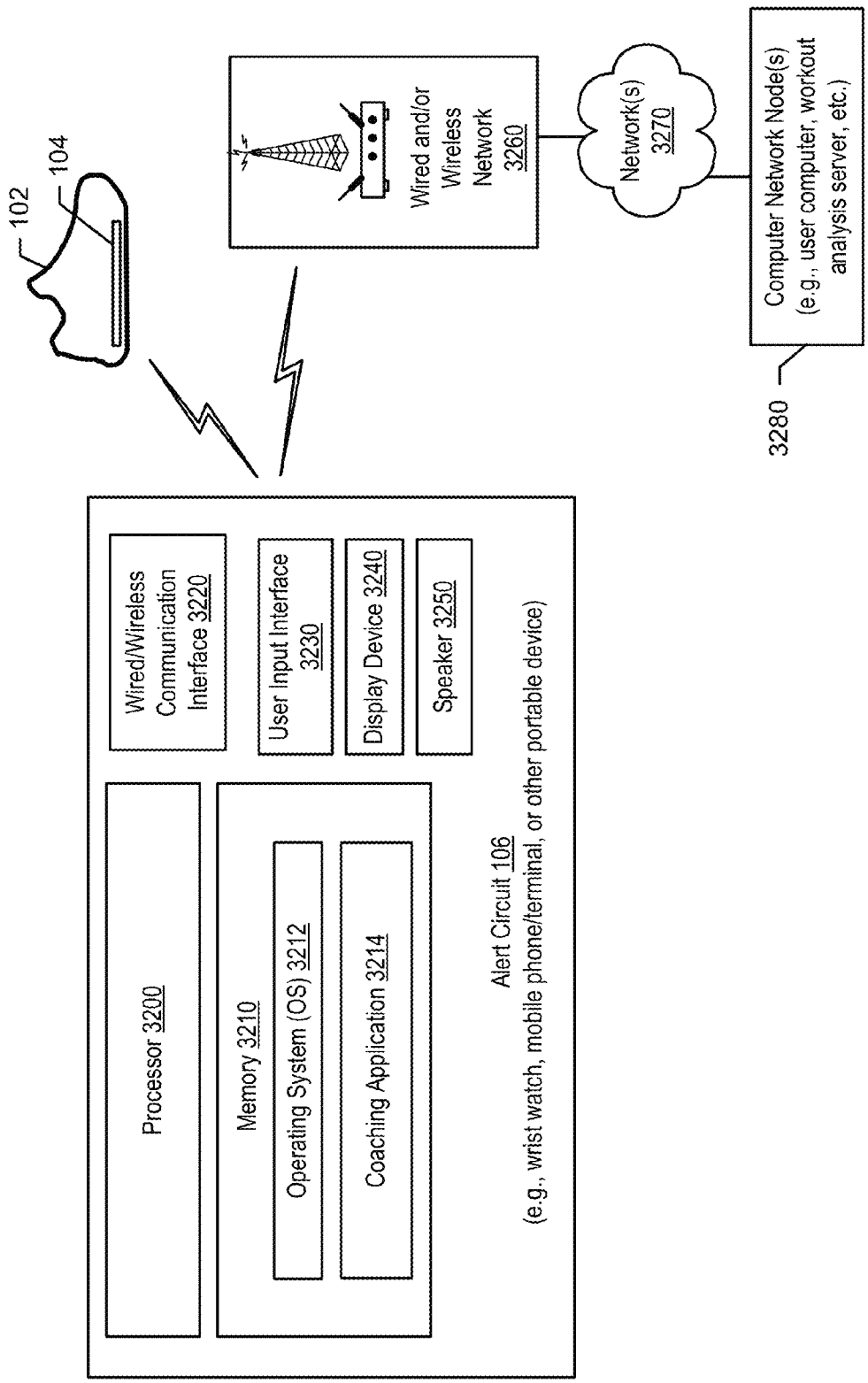
FIG. 33 illustrates a foot monitor system according to some embodiments of the present invention.

FIG. 33 illustrates a foot monitor system according to some embodiments of the present invention. The foot monitoring system includes an alert circuit 106 and a measurement circuit 104 within a shoe 102. The alert circuit 106 may, for example, be a wrist watch, mobile phone/terminal, or other portable device. The alert circuit 106 communicates with the measurement circuit 104 through a radio, magnetic, infra red, or other wireless communication interface. The alert circuit 106 may also communicate with a computer network node 3280 (e.g., the user computer, workout analysis server operated by equipment manufacturer (e.g., Garmin, Nike, Sony, Polar, etc.) or other entity, etc.) through a wired and/or wireless network interface 3260 (e.g., Bluetooth interface, WiFi router, other RF/IR/magnetic communication interface) and through one or more networks 3270 (e.g., local/wide area public/private networks).

The alert circuit 106 can include at least one processor 3200, at least one memory 3210, and at least one network interface 3220. The network interface 3220 may include a cellular transceiver, a wired network interface, a wireless local area network transceiver, a Bluetooth transceiver, a near field communication transceiver, and/or another wireless communication circuit. Accordingly although only one representative processor 3200, memory 3210, and network interface 3020 is illustrated in FIG. 33 for ease of illustration and explanation, is be understood that a plural number of processors, memories, and/or network interfaces may be used. The alert circuit 106 may further include a user input interface 3230, display device 3240, a speaker 3250, and/or other elements.

The processor 3200 may include one or more data processing circuits, such as a general purpose and/or special purpose processor (e.g., microprocessor and/or digital signal processor). The processor 3200 is configured to execute computer program instructions from the memory 3210, described below as a computer readable medium, to perform some or all of the operations and methods that are described herein for one or more of the embodiments disclosed herein. The memory 3210 can include an operating system (OS) 3212 (e.g., iOS by Apple, Android OS by Google, etc.) and a coaching application 3214 that is configured to perform operations and methods according to one or more embodiments disclosed herein. The coaching application 3214 may be downloaded from the computer network node 3280, which may be an application store such as the iTunes application store or the Android Marketplace application store.

Further Definitions Embodiments

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Exemplary embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks.

Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various exemplary combinations and subcombinations of embodiments and of the manner and process of making and using them, and shall support claims to any such combination or subcombination.

Many variations and modifications can be made to the embodiments without substantially departing from the principles of the present invention. All such variations and modifications are intended to be included herein within the scope of the present invention.

What is claimed:

1. A foot monitoring system comprising:
   a measurement circuit configured to measure sideways roll of a person's foot during at least a portion of forward rolling progression as the foot rolls forward from an impact location to lift-off from a running surface while the person is walking/running; and an alert circuit that is configured to:
determine based on the sideways roll that the person should change sideways spacing in a sideways direction between forward paths of the person's feet to change further measured values of the sideways roll of the person's foot toward preferred sideways roll values of the person's foot while the person continues walking/running; and generate a notification that indicates to the person to change the sideways spacing in the sideways direction between forward paths of the person's feet while the person continues walking/running.

2. The foot monitoring system of claim 1, wherein the alert circuit is configured to:
determine a relative distance based on a result of a difference between a measured value of the sideways roll and a baseline threshold value and/or based on a ratio of a measured value of the sideways roll and the baseline threshold value; and generate the notification based on the relative distance to indicate how far the person is recommended to change the sideways spacing in the sideways direction between forward paths of the person's feet while the person continues walking/running.

3. The foot monitoring system of claim 1, wherein the alert circuit is configured to:
receive input from the person indicating that a first spacing, corresponding to one of a greatest or a least sideways spacing between forward paths of the person's feet that the user finds acceptable for walking/running, is occurring;

record a measured value of sideways roll associated with the first spacing;

receive input from the person indicating that a second spacing, corresponding to the other one of the greatest or the least sideways spacing between forward paths of the person's feet that the user finds acceptable for walking/running, is occurring;

record a measured value of sideways roll associated with the second spacing;

determine a preferred value of sideways roll for the person based on the recorded measured values of sideways roll associated with the first and the second spacings; and generate notifications to the person to change sideways spacing in the sideways direction between forward paths of the person's feet based on comparison of the preferred value of sideways roll and measured values of sideways roll while the person continues walking/running.

4. The foot monitoring system of claim 3, wherein the alert circuit is configured to:
generate a notification that indicates to the person to change the sideways spacing between the greatest and the least sideways spacing between forward paths of the person's feet to perform calibration which generates the preferred value.

5. The foot monitoring system of claim 1, wherein the alert circuit is configured to:
determine at least one metric based on values of the measured sideways roll while the person walks/runs over a period of time for calibration;

determine a preferred value of sideways roll for the person's foot based on the at least one metric; and generate notifications that indicate to the person to change sideways spacing in the sideways direction between forward paths of the person's feet, based on comparison of the preferred value of sideways roll and measured values of sideways roll while the person continues walking/running.

6. The foot monitoring system of claim 5, wherein the alert circuit is configured to:
mathematically combine at least some of the measured values of sideways roll to generate the at least one metric; and determine the preferred value of sideways roll for the person's foot based on a mathematical combination of the at least one metric and body geometry information defined by the person or another operator that indicates whether the person walks/runs with overpronation sideways roll of the person's foot, neutral pronation sideways roll of the person's foot, or underpronation sideways roll of the person's foot.

7. The foot monitoring system of claim 5, wherein the alert circuit is configured to:
mathematically combine at least some of the measured values of sideways roll to generate the at least one metric; and determine the preferred value of sideways roll for the person's foot based on a mathematical combination of the at least one metric and body geometry information defined by the person or another operator that indicates an arch height of the person's foot.

8. The foot monitoring system of claim 5, wherein the alert circuit is configured to:
mathematically combine at least some of the measured values of sideways roll to generate the at least one metric; and determine the preferred value of sideways roll for the person based on a mathematical combination of the at least one metric and body geometry information defined by the person or another operator that indicates a length and/or width of the person's foot.

9. The foot monitoring system of claim 5, wherein the alert circuit is configured to:
determine a range of the values of the measured sideways roll as the person walks/runs over the period of time; and generate the preferred value of sideways roll based on the range of the values.

10. The foot monitoring system of claim 1, wherein:
the measurement circuit is configured to measure impact during at least a portion of forward rolling progression as the foot strikes the running surface and rolls forward from an impact location to lift-off from the running surface while the person is walking/running; and the alert circuit is configured to:
determine a relationship between values of the measured impacts and corresponding values of the measured sideways roll that are concurrently occurring;

determine a preferred value of sideways roll for the person's foot based on the relationship; and generate notifications to the person to change sideways spacing in the sideways direction between forward paths of the person's feet based on comparison of the preferred value of sideways roll and measured values of sideways roll while the person continues walking/running.

11. The foot monitoring system of claim 10, wherein the relationship determined by the alert circuit indicates a trend between changes in the values of the measured impacts and corresponding measured values of the sideways roll that are concurrently occurring.

12. The foot monitoring system of claim 11, wherein the alert circuit is configured to determine from the relationship the preferred value of sideways roll for the person to reduce values of the impacts while corresponding values of the sideways roll that are concurrently occurring satisfy a defined criteria as the person continues walking/running.

13. The foot monitoring system of claim 11, wherein the alert circuit is configured to determine from the relationship the preferred value of sideways roll for the person to obtain preferable values of the sideways roll while corresponding values of the impact that are concurrently occurring satisfy a defined criteria as the person continues walking/running.

14. The foot monitoring system of claim 1,
wherein the alert circuit is further configured to generate a record of values of the measured sideways roll of the person's foot while the person is walking/running; and
further comprising a display device configured to graph the values of the measured sideways roll from the record relative to an elapsed time of the activity, a speed at which the person was walking/running, a stride step distance, and/or a distance that the person walked/ran.

15. The foot monitoring system of claim 1, wherein the alert circuit is further configured to generate the notification by regulating a tone characteristic of an audible warning generated through a sound generation device to indicate to the person to change the sideways spacing in the sideways direction between forward paths of the person's feet while the person continues walking/running.

16. The foot monitoring system of claim 1, wherein the alert circuit is further configured to generate the notification by displaying a visual warning through a display device to indicate to the person to change the sideways spacing in the sideways direction between forward paths of the person's feet while the person continues walking/running.

17. The foot monitoring system of claim 1, wherein:
the measurement circuit is configured to be mounted on the person's shoe to increase sensitivity of the measurement from the foot striking the surface while the person is walking/running, and
the alert circuit comprises a wristwatch.

* * * * *